United States Patent [19]
Seidman et al.

[11] Patent Number: 5,912,121
[45] Date of Patent: Jun. 15, 1999

[54] METHODS FOR DETECTING MUTATIONS ASSOCIATED WITH HYPERTROPHIC CARDIOMYOPATHY

[75] Inventors: Christine Seidman; Jonathan Seidman, both of Milton; Ludwig Thierfelder, Brookline; Hugh Watkins, Brookline; Calum McRae, Brookline, all of Mass.

[73] Assignees: Bringham and Women's Hospital, Brookline; President and Fellows of Harvard College, Cambridge, both of Mass.

[21] Appl. No.: 08/354,326

[22] Filed: Dec. 12, 1994

Related U.S. Application Data

[63] Continuation of application No. 08/252,627, Jun. 2, 1994, abandoned, which is a continuation-in-part of application No. 07/989,160, Dec. 11, 1992, Pat. No. 5,429,923.

[51] Int. Cl.$^6$ .............................. C12Q 1/68; C12P 19/34; C07H 21/02; C07H 21/04
[52] U.S. Cl. ................................ 435/6; 435/5; 435/91.2; 536/23.1; 536/24.3; 536/24.31; 536/24.33
[58] Field of Search ................................... 435/5, 6, 91.2; 536/22.1, 23.1, 24.3, 24.21, 24.32, 24.33, 24.5

[56] References Cited

U.S. PATENT DOCUMENTS

| | | | |
|---|---|---|---|
| 4,736,866 | 4/1988 | Leder et al. | 800/1 |
| 5,046,499 | 9/1991 | Berger | 128/654 |
| 5,240,846 | 8/1993 | Collins et al. | 435/240.1 |
| 5,340,728 | 8/1994 | Grosz et al. | 435/91.2 |
| 5,429,923 | 7/1995 | Seidman et al. | 435/6 |

OTHER PUBLICATIONS

Stratagene catalog, p. 39, 1988.

Thierfelder et al, "a–tropomyosin and cardiac troponin T mutations cause familial hypertrophic cardiomyopathy: A disease of the sacromere", Cell 77:701–712, Jun. 1994.

Bonne et al., "Cardiac Myosin Binding Protein–C Gene Splice Acceptor Site Mutation is Associated With Familial Hypertrophic Cardiomyopathy," *Nature Genetics*, Dec. 1995, vol. 11, pp. 438–440.

Carrier et al., "Two New Mutations in the Cardiac C–Protein Gene Associated with Familial Hypertrophic CardioMyopathy are Predicted to Produce Truncated Proteins" *Circulation*, Oct. 15, 1996, vol. 94, No. 8, pp. 1426–1427, Abstract 2488.

Gautel et al., "Phosphorylation Switches Specific for the Cardiac Isoform of Myosin Binding Protein–C: a Modulator of Cardiac Contraction?" *The EMBO Journal*, vol. 14, No. 9, 1995, pp. 1952–1960.

Vikstrom et al., "Contractile Protein Mutations and Heart Disease" *Current Opinion in Cell Biology*, 1996, vol. 8, pp. 97–105.

Watkins et al., "Mutations In The Cardiac Myosin Binding Protein–C Gene On Chromosome 11 Causes Familial Hypertrophic Cardiomyopathy" *Nature Genetics*, Dec. 1995, vol. 11, pp. 434–437.

Anan, R. et al., "Prognostic Implications of Novel β Cardiac Myosin Heavy Chain Gene Mutations That Cause Familial Hypertrophic Cardiomyopathy," *J. Clin. Invest.*, vol. 93, 1–6, Jan. 1994.

Antonarakis, S.E., "Diagnosis of Genetic Disorders at the DNA Level," *New England Journal of Medicine*, vol. 320, No. 3, 153–163, Jan. 19, 1989.

Barrett et al., "Transgenic Animal Models of Cardiovascular Disease", *Current Opinion in Biotechnology*, vol. 3, 637–640, 1992.

Chelly, J. et al., "Transcription of the Dystrophin Gene in Human Muscle and Non–Muscle Tissues," *Nature*, vol. 333, 858–860, Jun. 30, 1988.

Cotton, R.G., "Detection of Single Base Changes in Nucleic Acids," *Biochem J.*, vol. 263, 1–10, 1989.

Davies, M.J., "Hypertrophic cardiomyopathy: one disease or several?" *British Heart Journal*, vol. 63, No. 5, 263–4, May 1990.

Epstein, N.D. et al., "Differences in Clinical Expression of Hypertrophic Cardiomyopathy Associated With Two Distinct Mutations in the β–Myosin Heavy Chain Gene," *Circulation*, vol. 86, No. 2, 345–352, Aug. 1992.

Geisterfer–Lowrance, A.A. et al., "A Molecular Basis for Familial Hypertrophic Cardiomyopathy: A β Cardiac Myosin Heavy Chain Gene Missence Mutation," *Cell*, vol. 62, 999–1006, Sep. 7, 1990.

(List continued on next page.)

*Primary Examiner*—Stephanie W. Zitomer
*Assistant Examiner*—Jeffrey Fredman
*Attorney, Agent, or Firm*—Giulio A. DiConti; Elizabeth A. Hanley

[57] ABSTRACT

The invention pertains to methods for detecting the presence or absence of a mutation associated with hypertrophic cardiomyopathy (HC). The methods include providing DNA which encodes a sarcomeric thin filament protein (e.g., α-tropomyosin or cardiac troponin T) and detecting the presence or absence of a mutation in the amplified product which is associated with HC. DNA encoding an actin-associated protein, a myosin-associated protein, or a sarcomeric protein other than β cardiac heavy chain can also be used in the methods of the present invention. The invention further pertains to methods for diagnosing familial HC (FHC) in a subject. These methods typically include obtaining a sample of DNA which encodes a sarcomeric thin filament protein from a subject being tested for FHC and diagnosing the subject for FHC by detecting the presence or absence of a mutation in the sarcomeric thin filament protein which causes FHC as an indication of the disease. An alternative method for diagnosing HC includes obtaining a sample of at least two sarcomeric proteins from a subject being tested for HC and diagnosing the subject for HC by detecting an abnormality in the sarcomeric proteins as an indication of the disease. Other aspects of the invention include kits useful for diagnosing HC and methods for treating HC.

24 Claims, 8 Drawing Sheets

OTHER PUBLICATIONS

Green, M.R., "Pre–mRNA Splicing," *Ann. Rev. Genet.*, vol. 20, 671–708, 1986.

Hardy, S. et al., "Characterization of muscle and non muscle *Xenopus laevis* tropomyosin mRNAs transcribed from the same gene," *Eur. J. Biochem.*, vol. 202, 431–440, 1991.

Ido, E. et al., "Kinetic Studies of Human Immunodeficiency Virus Type 1 Protease and Its Active–site Hydrogen Bond Mutant A28S," *Journal of Biological Chemistry*, vol. 266, No. 36, 24359–24366, 1991.

Jaencike, T. et al., "The Complete Sequence of the Human β–Myosin Heavy Chain Gene and a Comparative Analysis of Its Products," *Genomics*, vol. 8, 194–206, 1990.

Jarcho, J.A. et al., "Mapping a Gene for Familial Hypertrophic Cardiomyopathy to Chromosome 14q1," *New England Journal of Medicine*, vol. 321, 1372–1378, Nov. 16, 1989.

Keating, M., "Risk, Genotype, and Cardiovascular Disease," *Circulation*, vol. 86, No. 2, 688–690, Aug. 1992.

MacLeod, A.R. and C. Gooding, "Human hTMα Gene: Expression in Muscle and Nonmuscle," *Molecular and Cellular Biology*, vol. 8, 433–440, Jan. 1988.

MacRae et al., "An Evaluation of Ribonuclease Protection Assays for the Detection of –Cardiac Myosin Heavy Chain Gene Mutations", *Circulation*, vol. 89, No. 1, 33–35, Jan. 1994.

Madura, K. et al., "N–recognin/Ubc2 Interactions in the N–end Rule Pathway," *Journal of Biological Chemistry*, vol. 268, No. 16, 12046–12054, 1993.

Maron et al., "Patterns and Significance of Distribution of Left Ventricular Hypertrophy in Hypertrophic Cardiomyopathy," *American Journal of Cardiology*, vol. 48, 418–428, Sep. 1981.

McKenna et al., "Echocardiographic Measurement of Right Ventricular Wall Thickness in Hypertrophic Cardiomyopathy: Relation to Clinical and Prognostic Features," *JACC* vol. 11, No. 2, 351–8, Feb. 1988.

Mesnard et al. "Molecular Cloning and Developmental Expression of Human Cardiac Troponin T", *FEB Letters*, vol. 328, 139–144, Aug. 1993.

Miller, "Human Gene Therapy Comes of Age", *Nature*, vol. 357, 455–460, Jun. 11, 1992.

Myers, R. et al., "Detection of Single Bass Substitutions by Ribonuclease Cleavage at Mismatches in RNA: DNA Duplexes," *Science*, vol. 230, Dec. 13, 1985.

Oswald, M. and K. von der Helm, "Fibronectin is a non–viral substrate for the HIV protinase," *FEBS*, vol. 292, Nos. 1&2, 298–300, Nov. 1991.

Parker, T.G. and M.D. Schneider, "Growth Factors, Proto–Oncogenes, and Plasticity of the Cardiac Phenotype," *Ann. Rev. Physiol.*, vol. 53, 179–200, 1991.

Prasad, G.L. et al., "A cDNA Encoding a Muscle–Type Tropomyosin Cloned From a Human Epithelial Cell Line: Identify With Human Fibroblast Tropomyosin TM1," *Biochemical and Biophysical Research Communications*, vol. 177, No. 3, 1068–1075, Jun. 28, 1991.

Robberson, B.L. et al., "Exon Definition May Facilitate Splice Site Selection in RNAs with Multiple Exons," *Molecular and Cellular Biology*, vol. 10, No. 1, 84–94, Jan. 1990.

Roberts et al., "Direct Diagnosis of Carriers of Duchenne and Becker Muscular Dystrophy by Amplification of Lymphocyte RNA," *The Lancet*, vol. 336, 1523–1526, 22–29 Dec. 1990.

Rosenzweig, A. et al., "Preclinical Diagnosis of Familial Hypertrophic Cardiomyopathy by Genetic Analysis of Blood Lymphocytes," *New England Journal of Medicine*, vol. 325, 1753–1760, Dec. 19, 1991.

Ruiz–Opazo, N. and B. Nadal–Ginard,"α–Tropomyosin Gene Organization," *Journal of Biological Chemistry*, vol. 262, No. 10, 4755–4765, Apr. 5, 1987.

Saiki, R.K. et al., "Enyzmatic Amplification of β–Globin Genomic Sequences and Restriction Site Analysis for Diagnosis of Sickle Cell Anemia," *Science*, vol. 230, 1350–1354, Dec. 20, 1985.

Sarkar, G. and S. Sommer, "Access to a Messenger RNA Sequence or Its Protein Product Is Not Limited by Tissue or Species Specificity," *Science*, vol. 244, 331–334, Apr. 21, 1989.

Seidman, C.E. and J.G. Seidman, "Mutations in Cardiac Myosin Heavy Chain Genes Cause Familial Hypertrophic Cardiomyopathy," *Mol. Biol. Med.*, vol. 8, 159–166, 1991.

Shapiro, L. and W. McKenna, "Distribution of Left Ventricular Hypertrophy in Hypertrophic Cardiomyopathy: A Two Dimesional Echocardiographic Study," *JACC*, vol. 2, No. 3, 437–444, Sep. 1983.

Shoeman, R.L., et al., "Non–viral cellular substrates for human immunodeficiency virus type 1 protease," *FEBS*, vol. 278, No. 2, 199–203, Jan. 1991.

Solomon, S.D. et al., "Familial Hypertrophic Cardiomyopathy is a Genetically Heterogeneous Disease," *J. Clin. Invest.*, vol. 86, 993–999, Sep. 1990.

Takenaga, K. et al., "Isolation and Characterization of a cDNA That Encodes Mouse Fibroblast Tropomyosin Isoform 2," *Molecular and Cellular Biology*, vol. 8, No. 12, 5561–5565, Dec. 1988.

Tanigawa, G. et al., "A Molecualr Basis for Familial Hypertrophic Cardiomyopathy: An α/β Cardiac Myosin Heavy Chain Hybrid Gene," *Cell*, vol. 62, 991–998, Sep. 7, 1990.

Thierfelder et al., "Alpha–tropomyosin and Cardiac Troponin T Mutations Cause Familial Hypertrophic Cardiomyopathy: A Disease of the Sacromere", *Cell*, vol. 77, 701–712, Jun. 3, 1994.

Thierfelder, L. et al., "A familial hypertrophic cardiomyopathy locus maps to chromosome 15q2," *Proc. Natl. Acad. Sci. USA*, vol. 90, 6270–6274, Jul. 1993.

Watkins et.al., "A Disease Locus for Familial Hypertrophic Cardiomyopathy Maps to Chromosome 1q3", *Nature Genetics*, vol. 3, 333–337, Apr. 1993.

Watkins et al., "Characteristics and Prognosis Implications of Myosin Missense Mutations in Familial Hypertrophic Cardiomyopathy," *New England Journal of Medicine*, vol. 326, 1108–1114, Apr. 23, 1992.

Watkins et al. "Mutations in the Genes for Cardiac Troponin T and Alpha–tropomyosin in Hypertrophic Cardiomyopathy" *New England Journal of Medicine*, vol. 332; 1058–1064, Apr. 20, 1995.

Watkins et.al., "Sporadic Hypertrophic Cardiomyopathy Due to de Novo Myosin Mutations", *Journal of Clinical Investigation*, vol. 90, 1666–1671, Nov. 1992.

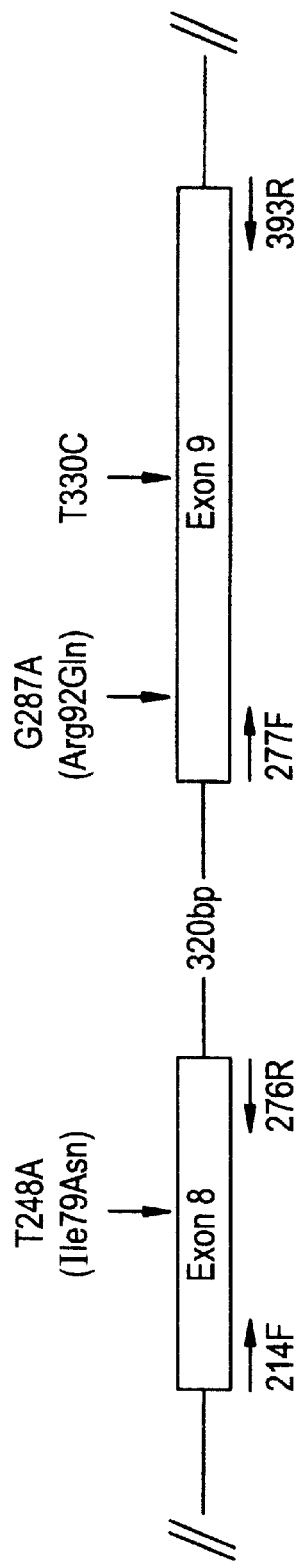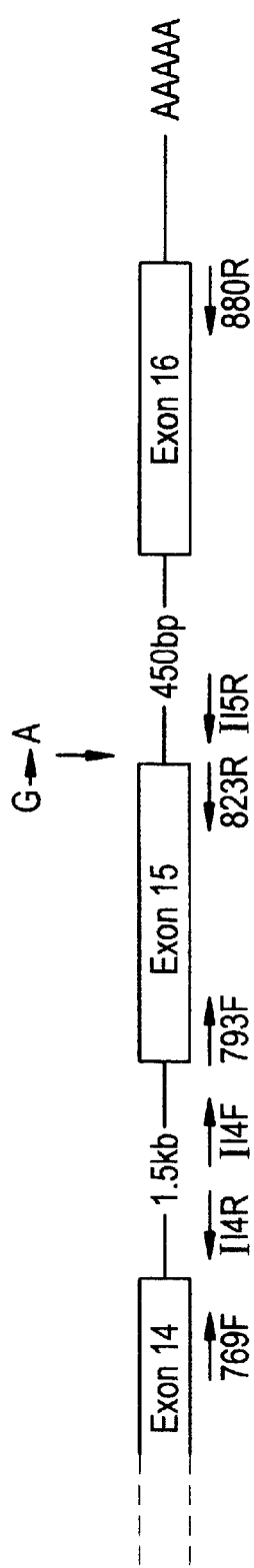

FIG. 5C

Genomic DNA

Exon 14
...CAGAAATATGAGgtggccgcgccatgtgtcccc -1.5kb- ccttccacttttcttgcagATCAATGTTCTCCGAAACAGGATCAACGATAACCAGAAAGTgtaagt
...GlnLysTyrGlu                                                   IleAsnValLeuArgAsnArgIleAsnAspAsnGlnLysVa
                                                                        793                          Exon 15              833  a Exon 16
gtctgaggtcattc -450bp- gcgtcctgctcccctgcagCTCCAAGACCCGGGGAAGGCTAAAGTCACCGGGCGCTGGAAATAGagcct...
                                           ISerLysThrArgGlyLysAlaLysValThrGlyArgTrpLys***

Mutant cDNAs

Exon 14
...CAGAAATATGAG][CTCCAAGACCCGGGGAAGGCTAAAGTACCGGGCGCTGGAAATAGagcct...
...GlnLysTyrGlu  LeuGlnLysLeuGlnAspProArgGluGly***

Exon 14                                    Exon 15
...CAGAAATATGAG][ATCAATGTTCTCCGAAACAGGATCAACGATAACCAGAAAGT][ataagtgtctgagCTCCAAGACCCGCGGGAA...
...GlnLysTyrGlu IleAsnValLeuArgAsnArgIleAsnAspAsnGlnLysVa l***

METHODS FOR DETECTING MUTATIONS ASSOCIATED WITH HYPERTROPHIC CARDIOMYOPATHY

RELATED APPLICATIONS

This application is a continuation of application Ser. No. 08/252,627 filed on Jun. 2, 1994, now abandoned which is a continuation-in-part of application Ser. No. 07/989,160 filed on Dec. 11, 1992, now U.S. Pat. No. 5,429,923 the contents of both of the aforementioned applications are hereby expressly incorporated by reference.

GOVERNMENT SUPPORT

This work was supported, in part, by National Institutes of Health grants HL46320 and HL42467.

BACKGROUND OF THE INVENTION

Familial hypertrophic cardiomyopathy (hereinafter FHC) is a primary and inherited disorder of heart muscle that is characterized by increased ventricular mass, hyperkinetic systolic function and impaired diastolic relaxation. Goodwin, J. F. et al. (1961) *Br. Med. J.* 21:69–79. The pathological features of this disorder are well established (Maron, B. J. and Epstein, S. E. (1980) *Amer. J. Cardiol.* 45:141–154). In addition to the classical finding of asymmetrical thickening of the intraventricular septum, hypertrophy of the adjacent left ventricular anterior free wall, apex or right ventricle can also occur. Hence the anatomical distribution and severity of hypertrophy can vary considerably. Maron, B. J. et al. (1981) *Amer. J. Cardiol.* 48:418–428. Fibrosis occurs within the hypertrophied ventricle and a fibrotic plaque is frequently demonstrable over the septal region that apposes the anterior mitral valve leaflet during systole. Other gross pathological findings include atrial dilation and thickening of the mitral valve leaflets. Roberts, W. C. and Ferrans, V. J. (1975) *Hum. Pathol.* 6:287–342.

The most characteristic histological abnormalities seen in FHC are myocyte and myofibrillar disarray. Davies, M. J. (1984) *Br. Heart J.* 51:331–336. Myocytes can be hypertrophied to ten to twenty times the diameter of a normal cardiac cell and may contain hyperchromatic, bizarre nuclei. Becker, A. E. (1989) Pathology of Cardiomyopathies in Cariomyopathies: Clinical Presentation, Differential Diagnosis, and Management (Shaver, J. A. ed.) F. A. Davis Co., New York, pp. 9–31. Cells are arranged in a disorganized fashion with abnormal bridging of adjacent muscle fibers and intercellular contacts, producing whorls. Ultrastructural organization is also distorted; myofibrils and myofilaments are disoriented with irregular Z bands. Ferrans, V. J. et al. (1972) *Circulation* 45:769–792. While the histopathological features overlap with those seen in hypertrophy that is secondary to other diseases, the extent of ventricular involvement and the severity of myocyte and myofibrillar disarray are considerably greater in FHC.

The pathology of FHC typically results in the physiological consequences of both systolic and diastolic dysfunction. Maron, B. J. et al. (1987) N. Eng. J. Med. 316:780–789. Systolic abnormalities include rapid ventricular emptying, a high ejection fraction and the development of a dynamic pressure gradient. Reduced left ventricular compliance results from an increase in the stiffness of the hypertrophied left ventricle and an increase in left ventricular mass. Impaired relaxation produces elevated diastolic pressures in the left ventricle as well as in the left atrium and pulmonary vasculature.

The clinical symptoms in individuals with FHC are variable and may reflect differences in the pathophysiological manifestations of this disease. Frank, S. and Braunwald, E. (1968) *Circulation* 37:759–788. Affected individuals frequently present with exertional dypsnea, reflecting the diastolic dysfunction that characterizes this disease. Angina pectoris is a common symptom, despite the absence of coronary artery disease. Ischemia may result from increased myocardial demand as well as inappropriately reduced coronary flow due to increased left ventricular diastolic pressures. Sudden, unexpected death is the most serious consequence of FHC, and occurs in both asymptomatic and symptomatic individuals.

The diagnosis of FHC relies on the presence of typical clinical symptoms and the demonstration of unexplained ventricular hypertrophy. Maron, B. J. and Epstein, S. E. (1979) *Amer. J. Cardiol.* 43:1242–1244; McKenna, W. J. et al. (1988) *J. Amer. Coll. Cardiol.* 11:351–538. Two-dimensional echocardiography and doppler ultrasonography are used to quantitate ventricular wall thickness and cavity dimensions, and to demonstrate the presence or absence of systolic anterior motion of the mitral valve. Electrocardiographic findings include bundlebranch block, abnormal Q waves and left ventricular hypertrophy with repolarization changes. Despite the existence of these detection tools, diagnosis of FHC can be difficult, particularly in the young, who may exhibit hypertrophy only after adolescent growth has been completed. Maron, B. J. et al. (1987) *N. Eng. J. Med.* 316:780–789.

Recently, genetic analyses have enabled identification of mutations in the β cardiac myosin heavy chain gene which are associated with FHC. Seidman, C. E. and Seidman, J. G. (1991) *Mol Biol. Med.* 8:159–166. The β cardiac myosin heavy chain gene encodes a sarcomeric thick filament protein. To date, genes encoding sarcomeric thin filament proteins have not been implicated in FHC.

SUMMARY OF THE INVENTION

The present invention is based, at least in part, on the discovery of mutations in the genes encoding the sarcomeric thin filament proteins α-tropomyosin and cardiac troponin T which cause HC and on the observation that defects in three contractile proteins: α-tropomyosin, cardiac troponin T, and β cardiac myosin heavy chain result in HC, demonstrating that this condition is a disease of the sarcomere.

The present invention provides methods for diagnosing individuals as having hypertrophic cardiomyopathy (hereinafter HC), e.g. familial or sporadic hypertrophic cardiomyopathy (hereinafter FHC or SHC). The methods provide a useful diagnostic tool which becomes particularly important when screening asymptomatic individuals suspected of having the disease. Symptomatic individuals have a much better chance of being diagnosed properly by a physician. Asymptomatic individuals from families having a history of FHC can be selectively screened using the method of this invention allowing for a diagnosis prior to the appearance of any symptoms. Individuals having the mutation responsible for FHC can be counseled to take steps which hopefully will prolong their life, i.e. avoiding rigorous exercise.

The invention pertains to methods for detecting the presence or absence of a mutation associated with HC. The methods include providing DNA which encodes a sarcomeric thin filament protein and detecting the presence or absence of a mutation in the DNA which is associated with HC. The methods can include amplifying the DNA (e.g., using a polymerase chain reaction, e.g., a nested polymerase chain reaction) to form an amplified product and detecting the presence or absence of mutations in the amplified product which are associated with HC. In one embodiment of the invention, the mutation associated with HC is detected by contacting the DNA with an RNA probe completely hybridizable to DNA which encodes a normal sarcomeric thin filament protein. The RNA probe and the DNA encoding a normal sarcomeric thin filament protein form a hybrid double strand having an unhybridized portion of the RNA strand at any portion corresponding to a hypertrophic cardiomyopathy-associated mutation in the DNA strand. The presence or absence of an unhybridized portion of the RNA strand can then be detected as an indication of the presence or absence of a HC-associated mutation in the corresponding portion of the DNA strand. These methods can optionally include contacting the hybrid double strand with an agent capable of digesting an unhybridized portion of the RNA strand prior to the detecting step. In addition, the methods can include providing DNA which encodes β cardiac myosin heavy chain for detection of mutations associated with HC.

Examples of thin filament protein DNA which can be analyzed using the methods of the invention include DNA which encodes α-tropomyosin and cardiac troponin T. The mutations in the DNA which encodes a sarcomeric thin filament protein can be point mutations (e.g., missense mutations) or splice site mutations. In one embodiment of the invention, the DNA which encodes a sarcomeric thin filament protein is cDNA reverse transcribed from RNA. An example of a source of RNA to be used as a template for reverse transcription is nucleated blood cells (e.g., lymphocytes).

The invention further pertains to methods for detecting the presence or absence of a mutation associated with HC (e.g., FHC or SHC) which include providing DNA which encodes an actin-associated protein and detecting the presence or absence of a mutation (e.g., a point mutation such as a missense mutation or a splice site mutation) in the DNA which is associated with HC. The methods can include amplifying the DNA (e.g., using a polymerase chain reaction, e.g., a nested polymerase chain reaction) to form an amplified product and detecting the presence or absence of mutations in the amplified product which are associated with HC. Examples of actin-associated protein DNA which can be used in the methods of the present invention include DNA which encodes α-tropomyosin and cardiac troponin T.

The invention still further pertains to methods for diagnosing FHC in a subject. The methods include obtaining a sample of DNA which encodes a sarcomeric thin filament protein from a subject being tested for FHC and diagnosing the subject for FHC by detecting the presence or absence of a mutation in the sarcomeric thin filament protein which causes hypertrophic cardiomyopathy as an indication of the disease. The method optionally includes amplifying the sarcomeric thin filament protein prior to the diagnosing step. In one embodiment of the invention, the sarcomeric thin filament protein is α-tropomyosin and the mutation is a point mutation. The point mutation can be a missense mutation in the α-tropomyosin DNA which results in an amino acid change at position 175 in α-tropomyosin such that aspartic acid is replaced with asparagine. Alternatively, the point mutation can be a missense mutation in the (α-tropomyosin DNA which results in an amino acid change at position 180 in α-tropomyosin such that glutamine is replaced with glycine. In another embodiment of the invention, the sarcomeric thin filament protein is cardiac troponin T and the mutation is a 5' splice site donor mutation. One location in which the 5' splice site donor mutation can occur is in intron 15 of cardiac troponin T DNA. In still another embodiment of the invention, the sarcomeric thin filament protein is cardiac troponin T and the mutation is a point mutation. The point mutation can be a missense mutation in the cardiac troponin T DNA which results in an amino acid change at position 79 such that isoleucine is replaced with asparagine. Another example of a point mutation is a missense mutation in the cardiac troponin T DNA which results in an amino acid change at position 92 such that arginine is replaced with glutamine. Exons suspected of containing the HC-causing mutation can be selectively amplified in the methods of the present invention.

Other aspects of the invention include methods for detecting the presence or absence of a mutation associated with HC (e.g., FHC or SHC) which include providing DNA which encodes a sarcomeric protein other than β-cardiac myosin heavy chain and detecting the presence or absence of a mutation in the DNA which is associated with HC. The methods can include amplifying the DNA (e.g., using a polymerase chain reaction, e.g., a nested polymerase chain reaction) to form an amplified product and detecting the presence or absence of mutations in the amplified product which are associated with HC. In one embodiment of the invention, the sarcomeric protein is α-tropomyosin and the mutation is a point mutation. The point mutation can be a missense mutation in the α-tropomyosin DNA which results in an amino acid change at position 175 in α-tropomyosin such that aspartic acid is replaced with asparagine. Alternatively, the point mutation can be a missense mutation in the α-tropomyosin DNA which results in an amino acid change at position 180 in α-tropomyosin such that glutamine is replaced with glycine. In another embodiment of the invention, the sarcomeric thin filament protein is cardiac troponin T and the mutation if a 5' splice site donor mutation. One location in which the 5' splice site donor mutation can occur is in intron 15 of cardiac troponin T DNA. In still another embodiment of the invention, the sarcomeric thin filament protein is cardiac troponin T and the mutation is a point mutation. The point mutation can be a missense mutation in the cardiac troponin T DNA which results in an amino acid change at position 79 such that isoleucine is replaced with asparagine. Another example of a point mutation is a missense mutation in the cardiac troponin T DNA which results in an amino acid change at position 92 such that arginine is replaced with glutamine.

Still other aspects of the invention include non-invasive methods for diagnosing HC. These methods typically include obtaining a blood sample from a subject being tested for HC (e.g., either FHC or SHC), isolating sarcomeric thin filament protein RNA from the blood sample, and diagnosing the subject for HC by detecting the presence or absence of a mutation in the RNA which is associated with FIC as an indication of the disease. In one embodiment of the invention, the presence or absence of a mutation associated with HC in the RNA is detected by preparing sarcomeric thin filament protein cDNA from the RNA to form sarcomeric thin filament DNA and detecting mutations in the DNA as being indicative of mutations in the RNA. The methods can optionally include amplifying the sarcomeric thin filament protein DNA prior to detecting a mutation in the DNA which is associated with HC and/or evaluating the subject for clinical symptoms associated with HC.

The invention also pertains to methods for determining the estimated life expectancy of a person having FHC. These methods include obtaining DNA which encodes a sarcomeric thin filament protein from a subject having FHC, detecting a mutation (e.g., a point mutation) in the DNA which encodes a sarcomeric thin filament protein which causes FHC, and estimating the life expectancy of the subject using a Kaplan-Meier curve for the classified type of mutation which causes FHC.

Other aspects of the invention include kits useful for diagnosing HC. The kits typically contain a first container holding an RNA probe completely hybridizable to DNA which encodes a sarcomeric thin filament protein (e.g., α-tropomyosin or cardiac troponin T). The kits can further optionally contain a second container holding primers useful for amplifying the DNA which encodes a sarcomeric thin filament protein. The kits can also optionally contain a third container holding an agent for digesting unhybridized RNA and/or instructions for using the components of the kits to detect the presence or absence of mutations in amplified DNA which encodes a sarcomeric thin filament protein.

The invention also provides kits for diagnosing HC which include a first container holding at least two RNA probes each of which is completely hybridizable to DNA which encodes a different sarcomeric protein. The kits can further optionally contain a second container holding primers useful for amplifying the DNA which encodes a sarcomeric thin filament protein. The kits can also optionally include a third container holding an agent for digesting unhybridized RNA and/or instructions for using the components of the kit to detect the presence or absence of mutations in amplified DNA which encodes a sarcomeric protein. In one embodiment of the invention, the kits contain a first RNA probe which is completely hybridizable to DNA which encodes Pcardiac myosin heavy chain and a second RNA probe which is completely hybridizable to DNA which encodes α-tropomyosin. These kits can also contain a third RNA probe which is completely hybridizable to DNA which encodes cardiac troponin T. Alternatively, the kits of the present invention contain a first RNA probe which is completely hybridizable to DNA which encodes β cardiac myosin heavy chain and a second RNA probe which is completely hybridizable to DNA which encodes cardiac troponin T. These kits can also contain a third RNA probe which is completely hybridizable to DNA which encodes α-tropomyosin.

Additional aspects of the invention include RNA probes which are complementary to at least a portion of DNA which encodes a sarcomeric protein other than β cardiac myosin heavy chain and sets of DNA primers for amplifying DNA which encodes a sarcomeric protein other than β cardiac myosin heavy chain. The primer sets typically include at least two, preferably four, oligonucleotides capable of amplifying DNA which encodes a sarcomeric protein other than β cardiac myosin heavy chain.

The invention also pertains to methods for diagnosing HC (e.g., FHC, SHC, or secondary cardiac hypertrophy) which include obtaining a sample of at least two sarcomeric proteins from a subject being tested for HC and diagnosing the subject for HC by detecting an abnormality in the sarcomeric proteins as an indication of the disease. Examples of such abnormalities include an abnormal stoichiometry in the sarcomeric proteins, expression of a nonfunctional or partially functional form of a sarcomeric protein, and lack of expression of a sarcomeric protein.

Other features of the present invention include methods for treating HC in a subject. These methods include adjusting an abnormal stoichiometry of sarcomeric proteins in a subject having HC to a normal stoichiometry of sarcomeric proteins in the subject. In one embodiment of the invention, the abnormal stoichiometry of the sarcomeric proteins is adjusted to a normal stoichiometry of sarcomeric proteins in the subject by administering to the subject a pharmacological agent which increases or decreases the expression of a sarcomeric protein.

The invention further features a non-human embryo comprising DNA which encodes a sarcomeric thin filament protein. The DNA contained in the nonhuman embryo has at least one hypertrophic cardiomyopathy-causing mutation in its nucleotide sequence.

The invention also features a non-human animal comprising DNA which encodes a sarcomeric thin filament protein. The DNA contained in the non-human animal has at least one hypertrophic cardiomyopathy-causing mutation in its nucleotide sequence.

Other aspects of the invention include methods for screening an agent for its ability to treat hypertrophic cardiomyopathy in a subject. These methods include providing a non-human animal comprising DNA which encodes a sarcomeric thin filament protein, the DNA having at least one hypertrophic cardiomyopathy-causing mutation in its nucleotide sequence, administering an agent being tested for its ability to treat hypertrophic cardiomyopathy in a subject to the non-human animal, and determining the effect of the agent on the hypertrophic cardiomyopathy in the non-human animal.

Further aspects of the invention include methods for treating hypertrophic cardiomyopathy in a subject. These methods include providing DNA which encodes a normal sarcomeric thin filament protein and administering the DNA to a subject having hypertrophic cardiomyopathy such that the hypertrophic cardiomyopathy is treated.

BRIEF DESCRIPTION OF THE DRAWINGS

FIGS. 4 Panels A and B, depict the structure of the human cardiac troponin T gene flanking exons 8 and 9 (Panel A) and exons 14–16 (Panel B). The positions of sequence variants are indicated by arrows above; the positions and orientation of primers are shown below. Approximate sizes of introns are given. The G→A transition (residue 1, intron 15) affects the 5' splice donor sequence.

DETAILED DESCRIPTION OF THE INVENTION

Figure 1:
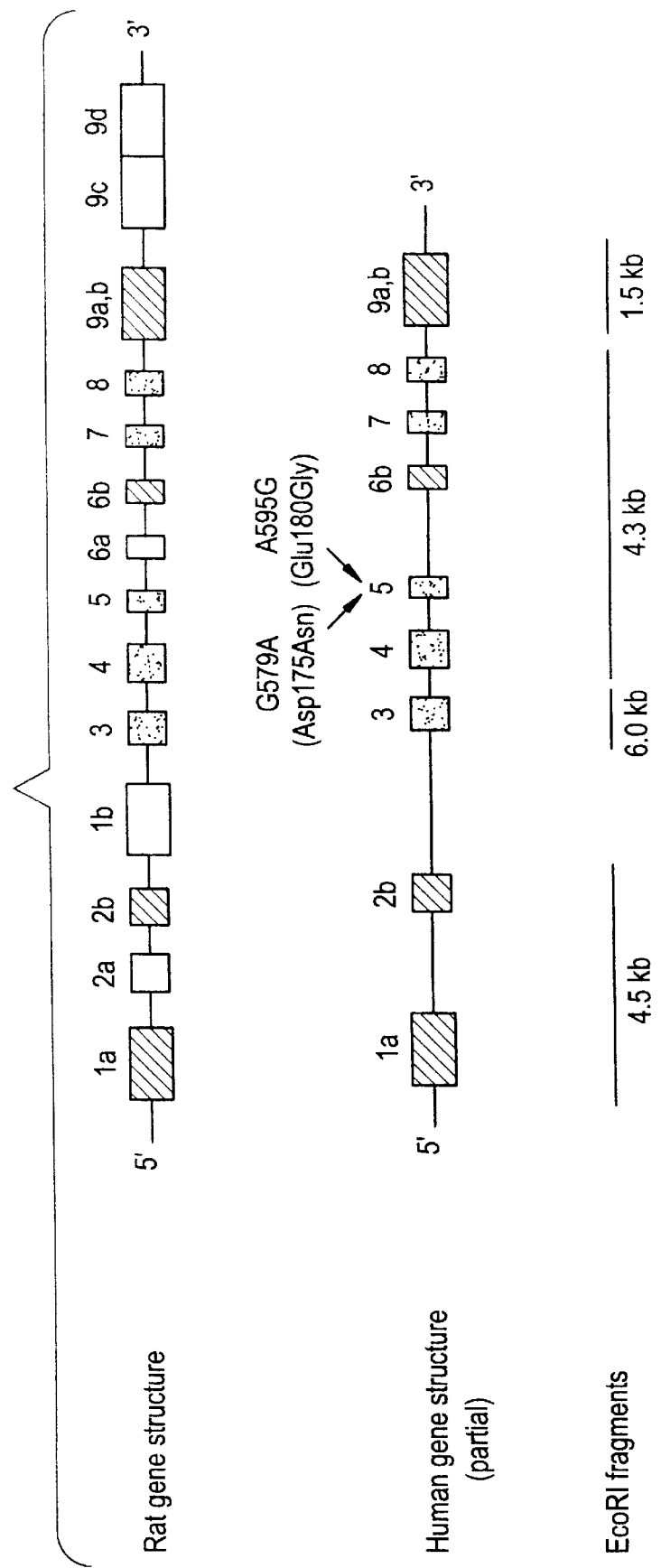
FIG. 1 depicts the genomic structure of the α-tropomyosin gene. The structure of the rat gene (Ruiz-Opazo, N. and Nadal-Ginard, B. (1987) *J. Biol. Chem.* 262:4755–4765) shows all potential exons: solid, constitutively expressed; stippled, expressed in striated muscle; clear, expressed in other tissues. The partial human gene structure was deduced from analyses of intron/exon boundaries corresponding to the striated muscle α-tropomyosin isoform. (The presence or absence of exons 1b, 2a, 6a, 9c and 9d in the human gene has not been studied.) The locations of FHC-causing mutations are indicated. Four EcoR1 fragments harboring the human striated muscle exons of α-tropomyosin are shown. Exons, the sizes of introns, and EcoR1 fragments are not drawn to scale.

The invention provides a method for detecting the presence or absence of a mutation associated with HC which comprises providing DNA which encodes a sarcomeric thin filament protein and detecting the presence or absence of a mutation in the DNA which is associated with HC. These methods can also include providing DNA which encodes β cardiac myosin heavy chain and detecting the presence or absence of mutations in the DNA which are associated with HC. The methods can further comprise amplifying the DNA (e.g., using a polymerase chain reaction, e.g., a nested polymerase chain reaction) to form an amplified product and detecting the presence or absence of mutations in the amplified product which are associated with HC.

For purposes of this invention, the term "mutation" is intended to include mutations associated with the respective diseases being discussed, e.g. HC. The mutation can be a gross alteration in the RNA or DNA or a small alteration in the RNA or DNA (e.g. a point mutation in the RNA or DNA). Examples of common mutations are deletions and insertions of nucleotides. The mutation further can be a mutation of the DNA which changes the amino acid encoded by that portion of the DNA strand, e.g. a missense mutation, or a mutation which does not change the encoded amino acid. The term mutation also specifically includes splice site mutations (e.g., 5' splice site donor mutations). Examples of missense mutations in the α-tropomyosin gene which cause HC include a mutation in exon 5 at position 595 of the α-tropomyosin gene wherein an adenine residue is replaced by a guanine residue. This adenine to guanine transition changes codon180 from GAG to GGG and predicts that a negatively charged glutamic acid residue is replaced by a neutral glycine residue. Another example of a missense mutation in the α-tropomyosin gene which causes HC is a mutation in exon 5 at position 579 of the α-tropomyosin gene wherein guanine is replaced by adenine. This guanine to adenine transition alters codon 175 from GAC to AAC, thereby predicting that a negatively charged aspartic acid residue is replaced with a neutral asparagine residue. Other examples of missense mutations which cause HC occur in the cardiac troponin T gene. These include a mutation at position 287 wherein guanine is replaced with adenine. This guanine to adenine transition changes codon 92 from CGG to CAG, predicting the replacement of a positively charged arginine with a neutral glutamine. A second missense mutation in the cardiac troponin T gene occurs at position 248 wherein thymidine is replaced with an adenine, resulting in an expected change to codon 79 from ATC to AAC, thereby replacing the normal nonpolar isoleucine residue with a polar asparagine residue. In addition, a 5' splice site donor mutation in intron 15 of the cardiac troponin T gene has been identified. See Examples and FIG. 5 for a detailed description of the 5' splice site donor mutation in intron 15 of the cardiac troponin T gene.

HC is a well characterized disorder or disease which is described in detail in the Background of the Invention section. This term is intended to include FHC, SHC and secondary cardiac hypertrophy. Mutations resulting in FHC are inherited throughout families and mutations resulting in SHC occur sporadically without a traceable hereditary path. For example, a subject having HC clinical symptoms may be diagnosed as having SHC if both of the subject's parents are actually diagnosed and determined to be healthy yet the subject has HC. Even further, if an afflicted subject's parents are not available for diagnosis and the afflicted subject has no other known family members with HC, then the subject probably would be diagnosed as having SHC. Secondary cardiac hypertrophy occurs in response to different stimuli (e.g., hypertension) and shares morphologic and histologic features with FHC.

The term "amplification" for purposes of this invention is intended to include any method or technique capable of increasing in number the respective DNA (including culturing) or RNA being discussed. The preferred amplification technique is the polymerase chain reaction (PCR) which is an art recognized technique and most preferably the amplification is conducted using a nested PCR technique as described in the examples below.

Figure 7A:
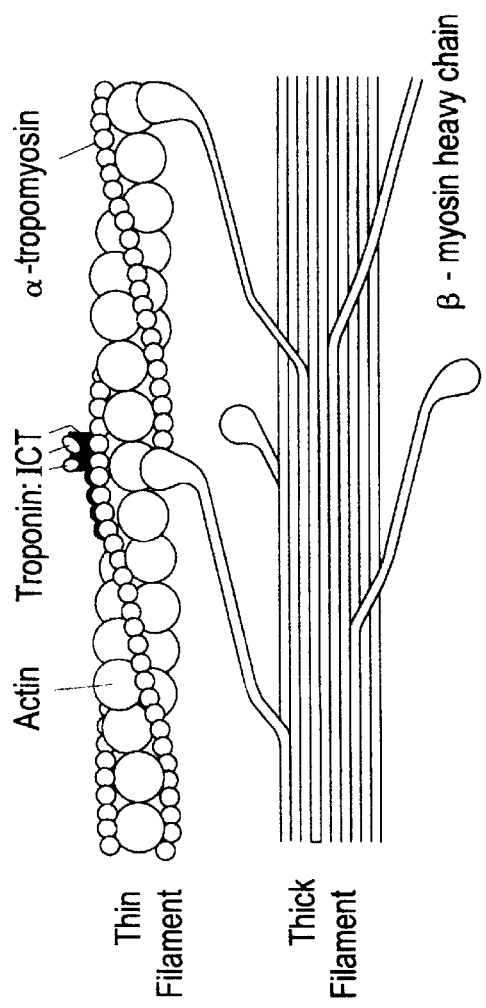
FIG. 7 Panels A–B, are a schematic representation of the sarcomere. Molecules in which FHC-causing mutations have been identified are darkened. Panel A is a longitudinal view of thick and thin filaments. The thin filament is composed of actin, α-tropomyosin, troponin I, C, T, and the thick filament includes myosin light chain (not indicated) and β cardiac myosin heavy chain (modified from Zot, A. S. and Potter, J. D. (1987) *Ann. Rev. Biophys. Chem.* 16:535–559). Panel B is a cross section of thin and thick filament interactions. $Ca^{2+}$ binding of troponin C causes the troponin-tropomyosin complex to release the myosin binding domain of actin; interaction of actin and myosin heads (on) then generates force.
Figure 7B:
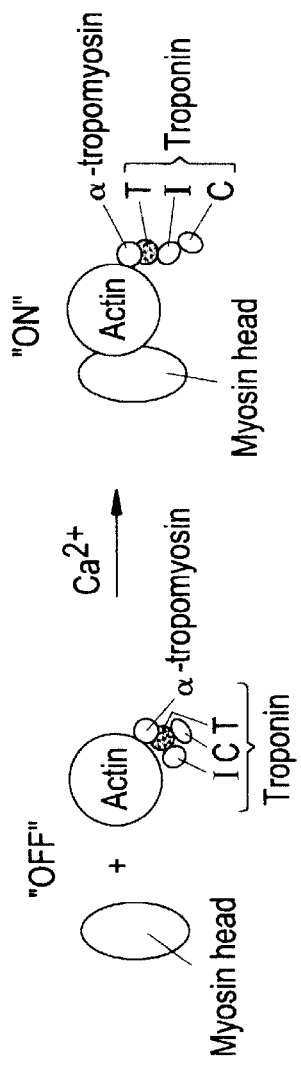

The phrase "DNA which encodes a sarcomeric thin filament protein" for purposes of this invention includes both genomic DNA which encodes a sarcomeric thin filament protein and cDNA which encodes a sarcomeric thin filament protein. The preferred DNA which encodes a sarcomeric thin filament protein is cDNA reverse transcribed from RNA obtained from a subject being screened for the respective disorder or disease, e.g. SHC or FHC. The RNA may be obtained from cardiac or skeletal tissue or from nucleated blood cells as described below. The DNA which encodes a sarcomeric thin filament protein encodes a protein which is a component of the thin filament in cardiac or skeletal tissue (i.e., muscle). Examples of components of cardiac or skeletal muscle thin filaments include actin, tropomyosin (see MacLeod, A. R. and Gooding, C. (1988) *Mol. Cell. Biol.* 8:433–440, reporting the structure of human cDNA sequence encoding the striated muscle isoform which is expressed in both cardiac and skeletal muscle tissues), and the troponin complex (including troponins C, T and I (FIG. 7) (see Mesnard, L. et al. (1993) *FEBS Lett.* 328:139–144, reporting the molecular cloning of human cardiac troponin T). Tropomyosin polypeptides form a helical coiled coil dimers of approximately 400 Å. These dimers arrange in a head to tail fashion, lie in the major groove of actin filaments, and span seven actin monomers. Amino acid residues 150–180 of α-tropomyosin constitute one of two putative troponin T binding domains that attach α-tropomyosin to the troponin complex (Zot, A. S. and Potter, J. D. (1987) *Ann. Rev. Biophys. Chem.* 16:535–559; White, S. P. et al. (1987) *Nature 325:826–828*). Both missense mutations in α-tropomyosin described above occur near the calcium-dependent troponin T-binding domain. In contrast, the missense mutations in cardiac troponin T described above are located in a region involved in calcium-insensitive binding to (α-tropomyosin. Brisson, J. -R. et al. (1986) *Biochemistry* 25:4548–4555; Pearlstone, J. R. et al. (1986) *J. Biol. Chem.* 267:16795–16810; Pan, B. -S. et al. (1991) *J. Biol. Chem.* 266:12432–12438. The splice site mutation alters the carboxyl terminus of cardiac troponin T, a region that contributes to calcium-dependent binding to tropomyosin. Ishii, Y. and Lehrer, S. S. (1991) *J. Biol. Chem.* 266:6894–6903. Each of these mutations produces a cardiac-specific phenotype.

Figure 5A:
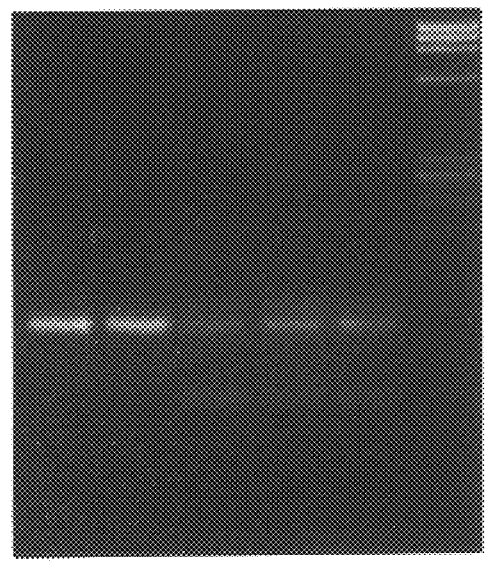
FIG. 5 Panels A–C, depict an analyses which revealed the identification of a 5' splice donor site mutation in affected individuals from family AU. Panel A shows troponin T cDNA amplified from lymphocyte RNA derived from normal (N) or affected (A) family members using primers 769F and 880R (FIG. 4). Samples from affected individuals contain the normal 111 bp product, a 70 bp product (resulting from exon 15 skipping), and a 124 bp product (resulting from activation of a cryptic splice site in intron 15). The size marker (M) is #X174/HaeIII. Panel B shows the nucleotide sequence of the exon 15/intron 15 boundary. The affected individual is heterozygous for the G→A transition at position 1 in intron 15 that disrupts the 5' splice donor site. Panel C shows the nucleotide sequences of genomic DNA and mutant cDNAs. Intron sequences are shown in lower case. A G→A transition (arrow) occurs in residue 1 of intron 15 at the 5' splice donor site. A cryptic splice donor site in intron 15 is underlined. The amino acids predicted to be encoded by the 3' end of two mutant troponin T cDNAs are shown with altered sequences in boldface. Skipping of exon 15 leads to loss of the terminal 28 amino acid residues, a frameshift encoding seven new residues and premature termination (triple asterisks). Activation of the cryptic splice donor site in intron 15 results in premature termination and loss of the terminal 14 amino acid residues.
Figure 5B:
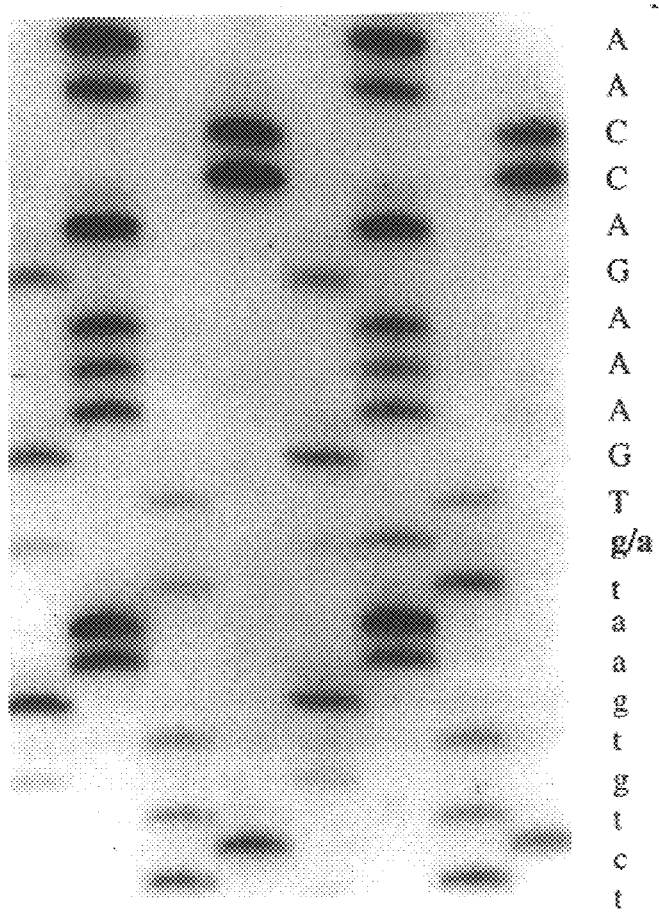

The 5' splice donor site mutation found in affected family AU members may also function as a null allele. The G→A transition at position 1 of intron 15 alters the universal 5' splice donor GT sequence and is expected to lead to aberrantly spliced mRNAs (Green, M. R. (1986) *Ann. Rev. Genet.* 20:671–708; Robberson, B. L. et al. (1990) *Mol. Cell. Biol.* 10:84–94). Two abnormal cDNA products were identified from lymphocyte RNAs that appear to reflect exon skipping and activation of a cryptic splice site (FIG. 5, Panel C). Both transcripts should encode a truncated peptide. The carboxy-terminal region of cardiac troponin T that is lost through this truncation is conserved in all species studied, including Drosophila (data not shown). Similar consequences of the donor splice site mutation in the myocardium most likely occur in humans. The splice donor site mutation in family AU is functionally is most likely a null allele of troponin T.

The phrase "DNA which encodes β cardiac myosin heavy chain" for purposes of this invention includes both genomic DNA which encodes β cardiac myosin heavy chain and cDNA which encodes β cardiac myosin heavy chain. The preferred β cardiac myosin heavy-chain DNA is cDNA reverse transcribed from RNA obtained from a subject being screened for the respective disorder or disease, e.g. SHC or FHC. The RNA may be obtained from cardiac or skeletal tissue or from nucleated blood cells as described below.

The detection of the presence or absence of a mutation associated with HC in an amplified product can be conducted using any method capable of detecting such mutations. Examples of conventional methods used to detect mutations in DNA sequences include direct sequencing methods (Maxim and Gilbert, (1977) *Proc. Natl. Acad. Sci. USA* 74:560–564; Sanger et al. (1977) *Proc. Natl. Acad. Sci. USA* 74:5463–5467 (1977)), homoduplex methods, heteroduplex methods, the single-stranded confirmation of polymorphisms (SSCP analysis) technique, and chemical methods. It should be understood that these methods are being provided merely to illustrate useful methods and one of ordinary skill in the art would appreciate other methods which would be useful in the present invention. The preferred detection method of the present invention is a heteroduplex method, particularly a protection assay which is similar to the RNase protection assay described by Myers et al. ((1985) *Science*, 230(3):1242–46), the contents of which are expressly incorporated herein by reference.

A protection assay can be used to detect the presence or absence of the HC-causing mutation by combining amplified sarcomeric thin filament protein DNA with an RNA probe under hybridization conditions forming a hybrid double strand. The RNA probe is selected to be completely hybridizable to DNA which encodes a normal sarcomeric thin filament protein, i.e. DNA without disease-causing mutatons. The hybridization conditions are the same or similar to those described by Myers et al., supra. For example, the hybridization can include the addition of the RNA probe to a solution containing the DNA, e.g. a hybridization buffer, at appropriate conditions, e.g. 90° C. for ten minutes. Subsequently, this mixture may be incubated for a longer period of time, e.g. at 45° C. for thirty minutes.

The term "completely hybridizable" for purposes of this invention is intended to include RNA probes capable of hybridizing at each nucleotide of a complementary normal DNA sequence. This characteristic of the RNA probe allows for the detection of an unhybridized portion at a mismatched or mutant nucleotide(s).

The hybrid double strand, i.e. the RNA:DNA double strand, has unhybridized portions of RNA at locations or portions corresponding to a mutation in the normal DNA strand, e.g. an HC-associated mutation. The hybrid double strand can be contacted with an agent capable of digesting an unhybridized portion(s) of the RNA strand, e.g. an RNase. The presence or absence of any unhybridized portions are then detected by analyzing the resulting RNA products. The RNA products can be analyzed by electrophoresis in a denaturing gel. Two new RNA fragments will be detected if the sample DNA contained a point mutation resulting in an unhybridized portion recognizable by the RNase. The total size of these fragments should equal the size of the single RNA fragment resulting from the normal DNA. The mutation(s) can be localized relative to the ends of the RNA probe by determining the size of the new RNA products. The sequence of the mutation may be determined by looking at the localized portion of corresponding DNA.

The agent capable of digesting an unhybridized portion of the RNA strand can be any agent capable of digesting unprotected ribonucleotides in the hybrid strands. Examples of such agents include ribonucleases, particularly RNase A.

As set forth above, the method of this invention can detect the presence or absence of the mutation associated with the respective disease or even further, the position within the gene or sequence of the mutation. The sequence or position can be determined by observing fragments resulting from mutations and comparing the fragments to a known template derived from the riboprobe which is representative of normal DNA.

The invention further pertains to methods for detecting the presence or absence of a mutation associated with hypertrophic cardiomyopathy which comprises providing DNA which encodes an actin-associated protein and detecting the presence or absence of a mutation in the DNA which is associated with hypertrophic cardiomyopathy. The methods can include amplifying the DNA (e.g., using a polymerase chain reaction, e.g., a nested polymerase chain reaction) to form an amplified product and detecting the presence or absence of mutations in the amplified product which are associated with HC.

DNA which encodes an actin-associated protein includes both genomic DNA which encodes an actin-associated protein and cDNA which encodes an actin-associated protein. The preferred DNA which encodes actin-associated proteins is cDNA reverse transcribed from RNA obtained from a subject being screened for the respective disorder or disease, e.g. SHC or FHC. The RNA can be obtained from cardiac or skeletal tissue or from nucleated blood cells as described below. The DNA which encodes an actin-associated protein encodes a protein, other than β cardiac myosin heavy chain, which is in contact with actin either transiently or permanently, or a protein, other than β cardiac myosin heavy chain, which is part of a protein complex which comes in contact with actin either transiently or permanently. Examples of actin-associated proteins include α-tropomyosin, the troponin complex, including troponins C, T and I, and components of myosin other than β-cardiac myosin heavy chain (e.g., myosin light chain). As used herein, the phrase "protein complex" includes an association, either covalent or noncovalent, of two or more proteins or protein fragments.

The invention still further pertains to methods for detecting the presence or absence of a mutation associated with hypertrophic cardiomyopathy which comprises providing DNA which encodes a myosin-associated protein and detecting the presence or absence of a mutation in the DNA which is associated with hypertrophic cardiomyopathy. The methods can include amplifying the DNA (e.g., using a polymerase chain reaction, e.g., a nested polymerase chain reaction) to form an amplified product and detecting the presence or absence of mutations in the amplified product which are associated with HC.

DNA which encodes a myosin-associated protein includes both genomic DNA which encodes a a myosin associated protein and cDNA which encodes a myosin-associated protein. The preferred DNA which encodes a myosin-associated protein is cDNA reverse transcribed from RNA obtained from a subject being screened for the respective disorder or disease, e.g. SHC or FHC. The RNA can be obtained from cardiac or skeletal tissue or from nucleated blood cells as described below. The DNA which encodes a myosin-associated protein encodes a protein, other than β cardiac myosin heavy chain, which is in contact with myosin either transiently or permanently, or a protein, other than β cardiac myosin heavy chain, which is part of a protein complex which comes in contact with myosin either transiently or permanently. Examples of myosin-associated proteins include myosin light chain and myosin binding proteins. As used herein, the phrase "protein complex" includes an association, either covalent or noncovalent, of two or more proteins or protein fragments.

The present invention also pertains to methods for diagnosing familial hypertrophic cardiomyopathy in a subject. These methods include obtaining a sample of DNA which encodes a sarcomeric thin filament protein from a subject being tested for familial hypertrophic cardiomyopathy and diagnosing the subject for familial hypertrophic cardiomyopathy by detecting the presence or absence of a mutation in the sarcomeric thin filament protein which causes hypertrophic cardiomyopathy as an indication of the disease. These methods can include an additional step of amplifying the sarcomeric thin filament protein DNA prior to the diagnosing step. Exons suspected of containing the HC-causing mutation can be selectively amplified.

The term "subject" for purposes of this invention is intended to include subjects capable of being afflicted with HC. The preferred subjects are humans.

Other aspects of the invention are methods for detecting the presence or absence of a mutation associated with HC which include providing DNA which encodes a sarcomeric protein other than β cardiac myosin heavy chain and detecting the presence or absence of a mutation in the DNA which is associated with HC. The methods can include amplifying the DNA (e.g., using a polymerase chain reaction, e.g., a nested polymerase chain reaction) to form an amplified product and detecting the presence or absence of mutations in the amplified product which are associated with HC.

DNA which encodes a sarcomeric protein other than β cardiac myosin heavy chain includes both genomic DNA which encodes a sarcomeric protein other than β cardiac myosin heavy chain and cDNA which encodes a sarcomeric protein other than β cardiac myosin heavy chain. The preferred DNA which encodes a sarcomeric protein other than β cardiac myosin heavy chain is cDNA reverse transcribed from RNA obtained from a subject being screened for the respective disorder or disease, e.g. SHC or FHC. The RNA can be obtained from cardiac or skeletal tissue or from nucleated blood cells as described below. The DNA which encodes a sarcomeric protein other than β cardiac myosin heavy chain encodes a protein, other than β cardiac myosin heavy chain, which is present in a sarcomere. Examples of sarcomeric proteins other than β cardiac myosing heavy chain include α-tropomyosin, the troponin complex, including troponins C, T and I, and components of myosin other than β-cardiac myosin heavy chain (e.g., myosin light chain). Although mutations in the β cardiac myosin heavy chain gene were known to cause HC, it was not known prior to the present discovery that HC can be caused by mutations in genes encoding other sarcomeric proteins. In fact, it was not known whether HC was a non-specific response to defects in myocyte function, a situation in which the disease genes would most probably encode unrelated proteins, or defects in the contractile apparatus, a situation in which the disease genes would probably encode sarcomeric proteins.

The present invention demonstrates that HC can be caused by mutations in two other genes encoding sarcomeric proteins (i.e., the genes encoding α-tropomyosin gene and cardiac troponin T) and, is, therefore, a disease of the sarcomere.

Other aspects of the present invention are non-invasive methods for diagnosing hypertrophic cardiomyopathy. The method involves obtaining a blood sample from a subject being tested for HC, isolating sarcomeric thin filament RNA from the blood sample, and diagnosing the subject for HC by detecting the presence or absence of a HC-associated mutation in the RNA as an indication of the disease. In one embodiment of the invention, the presence or absence of a mutation associated with HC in the RNA is detected by preparing sarcomeric thin filament protein cDNA from the RNA to form sarcomeric thin filament DNA and detecting mutations in the DNA as being indicative of mutations in the RNA. In this embodiment, the sarcomeric thin filament protein DNA can be amplified prior to detecting a mutation in the DNA which is associated with HC. The subject can be further evaluated for clinical symptoms associated with HC (some of which are described in detail in the Background of the Invention section).

The RNA can be isolated from nucleated blood cells. Nucleated blood cells include lymphocytes, e.g. T and B cells, monocytes, and polymorphonuclear leukocytes. The RNA can be isolated using conventional techniques such as isolation from tissue culture cells, guantidinium methods and the phenol/SDS method. See Ausebel et al. (Current Protocols in Molecular Biology (1991), Chapter 4, Sections 4.1–4.3), the contents of which are expressly incorporated by reference.

The present invention is partly based on the discovery that normal and mutant sarcomeric protein RNA is present in nucleated blood cells, e.g. lymphocytes, a phenomenon called ectopic transcription. Access to RNA provides a more efficient method of screening for disease-causing mutations because intron sequences have been excised from these transcripts. The present invention is a non-invasive method in that the mRNA is easily obtained from a blood sample.

The present invention also pertains to a method for determining the estimated life expectancy of a person having FHC. The method involves obtaining DNA which encodes a sarcomeric thin filament protein from a subject having FHC and detecting an FHC-causing point mutation. The point mutation subsequently is classified as a particular type and the life expectancy of the subject is estimated using a Kaplan-Meier curve for the classified type of mutation. Kaplan-Meier product-limit survival curves can be produced as described in Kaplan et al. (1958) J. Am. Stat. Assoc. 53:457–81; Lee, "Statistical Methods for Survival Data Analysis", Belmont, Calif., Lifetime Learning Publications, (1980)). See also copending U.S. Ser. No. 07/989,160, filed Dec. 11, 1992, the contents of which are expressly incorporated herein by reference.

The present invention also pertains to kits useful for diagnosing HC. The kits contain a first container such as a vial holding an RNA probe. The kits can further optionally contain a second container holding primers. The RNA probe is completely hybridizable to DNA which encodes a sarcomeric thin filament protein and the primers are useful for amplifying DNA which encodes a sarcomeric thin filament protein. The kits can further contain an RNA digesting agent and/or instructions for using the components of the kits to detect the presence or absence of HC-associated point mutation in amplified DNA encoding a sarcomeric thin filament protein.

The present invention additionally provides kits useful for diagnosing HC which include a first container holding at least two RNA probes each of which is completely hybridizable to DNA which encodes a sarcomeric protein. The kits can further optionally contain a second container holding primers useful for amplifying the DNA which encodes a different sarcomeric protein. The RNA probes in the kit are typically hybridizable to DNA which encodes β cardiac myosin heavy chain and DNA which encodes a different sarcomeric protein. For example, a kit of the present invention can contain RNA probes which hybridize to DNA which encodes β cardiac myosin heavy chain and DNA which encodes α-tropomyosin. This kit can optionally contain an additional RNA probe which hybridizes to a third sarcomeric protein such as cardiac troponin T. Alternatively, the kit of the present invention can contain RNA probes which hybridize to DNA which encodes β cardiac myosin heavy chain and DNA which encodes cardiac troponin T. This kit can optionally contain an additional RNA probe which hybridizes to a third sarcomeric protein such as α-tropomyosin. In another embodiment, the kits of the present invention can contain more than three RNA probes, each of which hybridizes to DNA which encodes a different sarcomeric protein. The kits further can further contain an RNA digesting agent and/or instructions for using the components of the kits to detect the presence or absence of HC-associated point mutation in amplified DNA encoding a sarcomeric thin filament protein.

The invention also features RNA probes which are complementary to at least a portion of DNA which encodes a sarcomeric protein other than β cardiac myosin heavy chain and a set of DNA oligonucleotide primers for amplifying DNA which encodes a sarcomeric protein other than β cardiac myosin heavy chain. The set of primers typically includes at least two oligonucleotides, preferably four oligonucleotides, capable of amplifying DNA which encodes a sarcomeric protein other than β cardiac myosin heavy chain.

Other aspects of the invention include methods for diagnosing HC which comprise obtaining a sample of at least two sarcomeric proteins from a subject being tested for HC and diagnosing the subject for HC by detecting an abnormality in the sarcomeric proteins as an indication of the disease.

The term "abnormality" is intended to include an inability of a sarcomeric protein to perform its intended function (e.g., enable cardiac muscle function). Examples of such abnormalities include an abnormal stoichiometry in the sarcomeric proteins, expression of a nonfunctional or partially functional form of a sarcomeric protein, and lack of expression of a sarcomeric protein.

As used herein, the phrase "abnormal stoichiometry" is intended to include a relative quantitative ratio of sarcomeric proteins which is different from a standard quantitative ratio (standard stoichiometry) of sarcomeric proteins. The standard stoichiometry of sarcomeric proteins is generated by collecting tissue samples from a population of subjects who are not believed to be afflicted with HC and determining the normal stoichiometric range of sarcomeric proteins in the samples. An abnormal stoichiometry of sarcomeric proteins can be detected by comparing the stoichiometry of at least two sarcomeric proteins of a tissue sample from a subject who is being tested for HC with the standard stoichiometry of the sarcomeric proteins described above.

A sample of sarcomeric proteins can be obtained directly from cardiac tissue by, for example, inserting a specialized catheter equipped with a grasper device (e.g., from Ethicon Inc., Cincinnati, Ohio), or the equivalent thereof, into a subject for positioning adjacent to the heart. The grasper device can then be used to remove a sample of the cardiac tissue. The sarcomeric proteins can then be isolated from the cardiac tissue and the quantity of each protein can be determined using methods known in the art (e.g., folin phenol method of Lowry, Rosebrough, Farr, and Randall, or a biuret reaction). See e.g., Creighton, T. E. Proteins:Structures and Molecular Properties (W. H. Freeman and Company, New York, 1984) pp. 26–28. The stoichiometry of the sarcomeric proteins is then easily ascertainable.

The invention also features methods for treating HC in a subject. These methods include adjusting an abnormal stoichiometry of sarcomeric proteins in a subject having HC to a normal stoichiometry of sarcomeric proteins in the subject. In one embodiment of the invention, the abnormal stoichiometry of the sarcomeric proteins is adjusted to a normal stoichiometry of sarcomeric proteins in the subject by administering to the subject a pharmacological agent which increases or decreases the expression of a sarcomeric protein.

Pharmacological agents which increase or decrease the expression of a sarcomeric protein include compounds which can regulate, alone or in combination with other compounds, the expression of a sarcomeric protein. Examples of such pharmacological agents include hormones and transcription factors. For example, it is known that thyroid hormone can regulate the expression of myosin and can, therefore, be administered to a subject to correct an abnormal stoichiometry of sarcomeric proteins which results from a deficiency in the expression of myosin. As described above, the 5' splice donor site mutation in the gene encoding cardiac troponin T may function as a null allele. The G→A transition at position 1 of intron 15 alters the universal 5' splice donor GT sequence and is expected to lead to aberrantly spliced mRNAs (Green, M. R. (1986) *Ann. Rev. Genet.* 20:671–708; Robberson, B. L. et al. (1990) *Mol. Cell. Biol.* 10:84–94). Thus, particularly useful pharmacological agents of the present invention include those agents which increase the expression of cardiac troponin T.

The pharmacological agent of the present invention can be administered to a subject through a route of administration which allows the pharmacological agent to perform its intended function, e.g. altering expression of a sarcomeric protein, at a level which is not detrimental to the subject. Examples of routes of administration which can be used include injection (subcutaneous, intravenous, parenteral, intraperitoneal, etc.), enteral, transdermal, and rectal. Depending on the route of administration, the agent can be coated with or in a material to protect it from the natural conditions which may detrimentally affect its ability to perform its intended function. The administration of the agent is done at dosages and for periods of time effective to significantly reduce or eliminate the symptoms associated with HC. Dosage regimes may be adjusted for purposes of improving the therapeutic response of the agent. For example, several divided doses may be administered daily or the dose may be proportionally reduced as indicated by the exigencies of the therapeutic situation.

Other aspects of the invention include non-human animal embryos comprising DNA which encodes a sarcomeric thin filament protein. The DNA which encodes a sarcomeric thin filament protein has at least one hypertrophic cardiomyopathy-causing mutation in its nucleotide sequence. Non-human embryos of the present invention can also contain DNA which encodes an actin-associated protein and which has at least one hypertrophic cardiomyopathy-causing mutation in its nucleotide sequence, DNA which encodes a myosin-associated protein and which has at least one hypertrophic cardiomyopathy-causing mutation in its nucleotide sequence, and DNA which encodes sarcomeric proteins other than β cardiac myosin heavy chain and which has at least one hypertrophic cardiomyopathy-causing mutation in its nucleotide sequence.

The term "non-human animal embryo" is intended to include a non-human fertilized embryo comprising at least one cell. Typically, a nonhuman embryo is derived from an animal of the class Mammalia. Examples of non-human mammals include dogs, cats, horses, cows, goats, rats, and mice.

The DNA can be introduced into the non-human embryo using any of the methods known in the art. Examples of well known methods of inserting DNA into a cell include calcium phosphate-mediated DNA transfection, electroporation, microinjection of the DNA into a non-human embryo, and virus-mediated delivery of the DNA to the embryo e.g. using retroviral vectors or adenovirus-based vectors.

The invention also pertains to non-human animals comprising DNA which encodes a sarcomeric thin filament protein, the DNA having at least one hypertrophic cardiomyopathy-causing mutation in its nucleotide sequence. Non-human animals of the present invention can also contain DNA which encodes an actin-associated protein and which has at least one hypertrophic cardiomyopathy-causing mutation in its nucleotide sequence, DNA which encodes a myosin-associated protein and which has at least one hypertrophic cardiomyopathy-causing mutation in its nucleotide sequence, and DNA which encodes sarcomeric proteins other than β cardiac myosin heavy chain and which has at least one hypertrophic cardiomyopathy-causing mutation in its nucleotide sequence.

The term "non-human animal" is intended to include an animal that is not a human. Typically, the non-human animal is a mammal such as a mouse or rat.

Still other aspects of the invention include methods for screening agents for their ability to treat hypertrophic cardiomyopathy in a subject. These methods include providing a non-human animal comprising DNA which encodes a sarcomeric thin filament protein, the DNA having at least one hypertrophic cardiomyopathy-causing mutation in its nucleotide sequence, administering an agent being tested for its ability to treat hypertrophic cardiomyopathy in a subject to a the non-human animal, and determining the effect of the agent on the hypertrophic cardiomyopathy in the nonhuman animal.

The agent being tested for its ability to treat hypertrophic cardiomyopathy can be administered to a subject at a level which is not detrimental to the subject. Examples of routes of administration which can be used include injection (subcutaneous, intravenous, parenteral, intraperitoneal, etc.), enteral, transdermal, and rectal.

The phrase "an agent being tested for its ability to treat hypertrophic cardiomyopathy" is intended to include a compound which can be tested to determine its ability to reduce, eliminate, or prevent the detrimental effects of HC on a subject.

The phrase "determining the effect of the agent on the HC in the non-human animal" is intended to include ascertaining whether the agent reduces, eliminates, or prevents the detrimental effects of HC on a subject or whether the agent has no effect on the detrimental effects of HC on a subject.

The term "treat" as used herein is intended to include reduction, elimination, or prevention of the detrimental effects (e.g., symptoms) of HC on a subject. Many of these detrimental effects are described in detail in the Background of the Invention section.

The invention further pertains to methods for treating hypertrophic cardiomyopathy in a subject comprising administering DNA which encodes a normal sarcomeric thin filament protein to a subject having hypertrophic cardiomyopathy such that the hypertrophic cardiomyopathy is treated. DNA which encodes a normal actin-associated protein, DNA which encodes a normal myosin-associated protein, and DNA which encodes a normal sarcomeric proteins other than β cardiac myosin heavy chain can be also be administered to subject having HC. These methods typically include packaging the DNA in a carrier such as a plasmid, phage (e.g., bacteria phage lambda), virus, or a lipid vesicle for enabling introduction of the DNA into a cell of the subject. Examples of viruses that are commonly used to deliver DNA to a target cell include retroviruses and vaccinia viruses. Preferred DNA carriers include viruses such as adenovirus and adeno-associated viruses. Examples of lipid vesicles include detergent or other amphipathic molecule micelles, membrane vesicles, liposomes, virosomes, and microsomes.

Lipid vesicles can also be used to deliver a normal sarcomeric thin filament protein, a normal actin-associated protein, a normal myosin-associated protein, or a normal sarcomeric protein other than β cardiac myosin heavy chain to a cell of a subject having hypertrophic cardiomyopathy such that the hypertrophic cardiomyopathy is treated.

The term "normal" as used herein is intended to refere to a protein which performs its intended function. Normal proteins do not contain mutations which detrimentally effect the intended function of the protein.

The present invention is further illustrated by the following Examples which in no way should be construed as further limiting. The entire contents of all of the references (including literature references, issued patents, published patent applications, and co-pending patent applications) cited throughout this application are hereby expressly incorporated by reference. The entire contents of Rozensweig, A. et al. (1991) N. Eng. J. Med. 325:1753–60 (Dec. 19, 1991)) and Watkins, H. et al. (1992) N. Eng. J. Med. 326:1108–1114 also are expressly incorporated by reference.

THE FOLLOWING MATERIALS AND METHODS APPLY TO THE EXAMPLES

Clinical evaluation:

Clinical evaluations of Families AW and BA were performed as previously described for Families MZ and MI from Freiburg and Bad Nauheim (Thierfelder, L. et al. (1993) Proc. Natl. Acad. Sci. USA 90:6270–6274) and Family AU (Watkins, H. et al. (1993) Nature Genet. 3:333–337). At the time of clinical evaluation, a blood sample was obtained for all genetic analyses.

Isolation of the human α-tropomyosin gene:

A human P1 library (Pierce, J. and Stemberg, N. (1992) Meth. Enzymol. 216:549–574) was screened by PCR amplification of a 126 bp fragment of the 3' untranslated region of the human α-tropomyosin gene (MacLeod, A. R. and Gooding, C. (1988) Mol. Cell. Biol. 8:433–440) using primers: forward: 5'-AGC TGG ATG TCC CAC CTC T-3' (SEQ ID NO:1); reverse: 5'-ACG AAG AGC TTC TGT ACA ATA G-3' (SEQ ID NO:2). One clone, designated HTMα, was identified and purified using a combination of PCR-based and filter hybridization techniques.

Identification of a $CA_{17}$ STR in the HTMα P1 clone:

500 ng of HTMα DNA was hybridized to an alkaline phosphatase-linked CA oligonucleotide (QUICK LIGHT™ Hybridization Kit, FMC) to detect an STR, designated $HTMα_{CA}$. 2 to 5 μg of HTMα DNA were then digested with Sau3A, blotted, and hybridized to the CA oligonucleotide probe. DNA fragments (sized approximately 250 bps) containing a $(CA)_n$ repeat were subcloned. Three clones encoding a $(CA)_{17}$ motif were sequenced. Based on flanking sequence, primers surrounding the $HTMα_{CA}$ were constructed: forward: 5'-GAG TCA GAT GTT CCA ATA AGG TAG G-3' (SEQ ID NO:3) reverse: 5'-TGT CTT GCT CCC TAC CCT CTG TGA-3' (SEQ ID NO:4). The predicted length of the amplified $HTMα_{CA}$ was 114 bp.

Intron/exon boundaries in the human a tropomyosin gene:

2 to 5 μg DNA of the P1 clone HTMα were digested with EcoR1, size-fractionated on an agarose gel, and transferred to a nylon filter. Using primers corresponding to a human striated muscle α-tropomyosin cDNA (MacLeod, A. R. and Gooding, C. (1988) Mol. Cell. Biol. 8:433–440), two cDNA fragments were amplified from human ventricular RNA and cloned into Bluescript. These cDNA fragments were labeled with $^{32}P$ and used to probe the HTMα genomic EcoR1 fragments. Four DNA fragments, ranging in size from 1.5 to 6.0 kb (FIG. 1), that hybridized to the cardiac cDNA clones were subcloned.

Sequences within the nine exons (1a, 2b, 3, 4, 5, 6b, 7, 8, and 9 a,b) encoded in striated muscle isoforms of a tropomyosin were used to construct primers. Primers were used to sequence EcoR1 subclones of HTMα. Based on flanking intron sequences the following primers were constructed: exon 1a (forward): 5'-CCG GAA TTC TGC TGC AGC CCC AGG CCC CT-3' (SEQ ID NO:5); exon 1a (reverse): 5'-GGT GCC AGG CTC GAG TCC CG-3' (SEQ ID NO:6); exon 2b (forward): 5'-TCC CTG TAC CCC CTG GCC AA-3' (SEQ ID NO:7); exon 2b (reverse): 5'-CGC GGA TCC GGG AAG CAG TGT GAG CGT GC-3' (SEQ ID NO:8); exon 3 (forward): 5'-CCC AGC CAT TTC CTG AAG CTA CCA-3' (SEQ ID NO:9); exon 3 (reverse): 5'-CCA CCA GGA AAG GCA GCT GCA AAA G-3' (SEQ ID NO:10); exon 4 (forward): 5'-GGC CAC AGC AGT GCA GTG TGC ATT T-3' (SEQ ID NO:11); exon 4 (reverse): 5'-GGC TGT CCT GAA GGC CAC TGC T-3' (SEQ ID NO:12); exon 5 (forward): 5'-CCA TGC CCT TCT GTT ACA CAA AGC-3' (SEQ ID NO:13); exon 5 (reverse): 5'-TGC CAG AAG GTC ATG CTG TTT AGT C-3' (SEQ ID NO:14); exon 6b (forward): 5'-TTG GCT TGT CTC CCA CCC TT-3' (SEQ ID NO:15); exon 6b (reverse): 5'-GGC CTC TTT TGA GCA GCT CTT AAA AG-3' (SEQ ID NO:16); exon 7 (forward): 5'-GAG TAG ATT GAG CAG CAG CTT GAC A-3' (SEQ ID NO:17); exon 7 (reverse): 5'-ATG AAA AGG CCT GAC CGG TTC CAT G-3' (SEQ ID NO:18); exon 8 (forward): 5'-CCC TAT GTT TGT AGC TAC AGG AAA C-3' (SEQ ID NO:19); exon 8 (reverse): 5'-AGT GCA AAG GAG CGT ATC AAT GTG G-3' (SEQ ID NO:20); exon 9a,b (forward): 5'-TCT GCC TTC CAC TTC CTG GT-3' (SEQ ID NO:21); exon 9a,b (reverse): 5'-CAA GGA GGC ATG GTG GTG AGT TTA-3' (SEQ ID NO:22).

Screening the α-tropomyosin gene for mutations:

Each of the nine exons encoded in the striated muscle-specific isoform of the α-tropomyosin gene was amplified from DNA derived from family members or unrelated individuals using the following conditions. Exon 1: 40 rounds of amplification (94° C. for 20 seconds, 72° C. for 40 seconds); Exons 2–9a, b: 35 rounds of amplification (94° C. for 20 seconds, 55°–58° C. for 20 seconds, and 72° C. for 40 seconds). Each PCR product (1–3 μl) was then cycle sequenced using the corresponding forward or reverse $[\gamma^{32}P]$ ATP end-labeled primer (Cyclist™ Taq DNA Sequencing Kit, Stratagene).

Oligonucleotide primers for cardiac troponin T cDNA

All oligonucleotide primers indicated in the specification and in FIG. 4 were 25mers, identified by the position of the 5' residue and numbered according to Mesnard, L. et al. (1993) *FEBS Lett.* 328:139–144.

PCR screening of somatic cell hybrids

A panel of rodent-human somatic cell hybrids was obtained from the National Institute of General Medical Sciences Human Genetic Mutant Cell Repository (NIGMS mapping panel #2); in addition two hybrids with fragments of chromosome 1 were analyzed (GM 11526A, GM 11130). Amplification by PCR was performed with 50 ng of hybrid DNA and primers 894F and 1002R.

Amplification of troponin T cDNA from lymphocyte RNA

Using previously described methods (Rosenzweig, A. et al. (1991) *N. Engl. J. Med.* 325:1753–1760), two micrograms of total RNA obtained from Epstein Barr virus-transformed lymphocytes were reverse transcribed using Moloney murine leukemia virus reverse transcriptase and an oligo(dT) primer in a 20 $\mu$l volume; the cDNA products were then amplified in a 100 $\mu$l PCR reaction using the outer primer pair 1F and 1002R. The second round of PCR was performed with a final dilution of 1:1000 of the first round products, using either primers 1F and 570R or primers 523F and 915R.

RNase A protection assays

RNase A protection assays for the detection of sequence differences in amplified cDNAs were performed as previously described (Watkins, H. et al. (1992) *N. Engl. J. Med.* 326:1108–1114). Riboprobes were prepared from subcloned normal myocardial cDNA products 1–570 and 523–915. All sequences were hybridized with both sense and antisense riboprobes.

Cycle sequencing of PCR products

PCR-amplified troponin T cDNA or genomic DNA fragments were sequenced using the Cyclist™ Taq DNA Sequencing Kit (Stratagene). PCR products were precipitated to remove residual primers but were not gel isolated. The primer for sequencing (usually the one that had been used for the amplification) was end-labeled to high specific activity with [$\gamma^{32}$P]ATP. Typically, for each sequencing reaction the equivalent of 1 $\mu$l PCR product was cycled with 8 ng of primer. For detection of the G→A transition in intron 15 in family AU members and controls, a genomic fragment (793-880) was sequenced with primer 793F using only ddATP to detect the presence or absence of the mutant adenine residue.

Amplification of troponin T sequences from genomic DNA

The primers used for amplification and sequencing of exons 8, 9, 14, 15 and 16 (FIG. 4) were derived from the human cDNA sequence (Mesnard, L. et al. (1993) *FEBS Lett.* 328:139–144) positioned according to the exon-intron boundaries of the rat troponin T gene (Jin, J. P. et al. (1992) *J. Mol. Biol.* 227:1269–1276). Three primers were then synthesized from intronic sequence for sequencing exon/intron boundaries: I14 reverse: 5'-CCC AGG GAC CTG CAG CAG TAT TAC C-3' (SEQ ID NO:23); I14 forward: 5'-TCA GCT CCA CGT TGC TCT TTG TCC T-3' (SEQ ID NO:24); I15 reverse: 5'-AAG GAG GAA TGG GAT AGC TGG AAG G-3'. (SEQ ID NO:25).

Linkage analyses:

The HTM$\alpha_{CA}$ was amplified from genomic DNA by PCR as described previously (Chou, Y. et al. (1992) *Nature Genet.* 1:295–300). The frequencies of the five HTM$\alpha_{CA}$ alleles that were observed in families MZ and MI were estimated from spouses.

The restriction fragment length polymorphism (RFLP) in exon 9 of cardiac troponin T was amplified from genomic DNA using oligonucleotide primers 277F and 393R (FIG. 4, Panel A) and digested with TaqI. The heterozygosity index for the T330C polymorphism was estimated as 0.4 from genotypes of spouses (data not shown). Linkage analyses were performed with allele frequencies of T=0.75 and C=0.25.

Linkage between FHC and each gene was assessed by calculating two point lod scores in each family using the computer program MLINK (Ott, J. (1967) *Am. J. Hum. Genet.* 28:528–529) and assuming a disease penetrance of 95%.

EXAMPLE 1

IDENTIFICATION OF MUTATIONS IN THE α-TROPOMYOSIN GENE

Mapping the human α-tropomvosin gene to CMH3

The murine gene encoding a tropomyosin was recently mapped to mouse chromosome 9, adjacent to a syntenic region of human chromosome 15q (Schleef, M. et al., (1993) *Genomics* 17:519–521). To assess linkage between the human α-tropomyosin gene and CMG3 on chromosome 15q2, a short tandem repeat polymorphism (STR) was identified. A human P1 library (Pierce, J. and Sternberg, N. (1992) *Meth. Enzymol.* 216:549–574) was screened with a 126 bp cDNA fragment corresponding to the 3' untranslated region of the human α-tropomyosin gene (MacLeod, A. R. and Gooding, C. (1988) *Mol. Cell. Biol.* 8:443–440). One P1 clone (designated HTMα) containing all of the structural portions of the α-tropomyosin gene was isolated and screened for STR motifs (See Materials and Methods). A CA$_{17}$ repeat (designated HTMα$_{CA}$) was identified and the flanking nucleotide sequences determined to synthesize corresponding primer pairs (Materials and Methods). Five alleles of HTMα$_{CA}$ were identified.

FHC in two families, MZ and MI, was previously shown to be linked to CMH3 (Thierfelder, L. et al. (1993) *Proc. Natl. Acad. Sci. USA* 90:6270–6274). Linkage between HTMα$_{CA}$ and FHC was demonstrated in these families (data not shown). Four members of family MZ and one member of family MI were previously recognized to have haplotypes at multiple polymorphic loci near CMG3 that were discordant with their clinical unaffected status. In the present study, these individuals were assumed to have a nonpenetrant FHC mutation and were considered to have an unknown disease status for lod score calculations. A maximum two point lod score of 4.60 at θ=0 was achieved between FHC and HTMα in family MZ; in family MI the maximum two point lod score was at 2.34 (at q=0). The combined maximum two point lod score of 6.94 (at θ=0) showed that the human gene encoding a tropomyosin was closely linked to CMH3.

Identification of missense mutations in the α-tropomyosin gene

The vertebrate α-tropomyosin gene consists of 15 exons; 5 exons are found in all transcripts, while 10 exons are alternatively used in different α-tropomyosin RNAs (Lees, M. J. and Helfman, D. M. (1991) *Bioessays* 13:429–437). Although the structure of a human cDNA sequence encoding the striated muscle isoform has been determined (MacLeod, A. R. and Gooding, C. (1988) *Mol. Cell. Biol.* 8:433–440), the organization of the human gene is unknown. The striated muscle isoform is expressed in both cardiac and skeletal muscle tissues. Human and rat striated muscle α-tropomyosin (Ruiz-Opazo, N. and Nadal-Ginard, B. (1987) *J. Biol. Chem.* 262:4755–4765) share 99.6% amino acid identity.

To determine whether a defect in the (α-tropomyosin gene caused FHC in affected members of families MZ and MI, all exons expressed in striated muscle were screened for mutations. Portions of subcloned HTMα were sequenced to define the intron/exon boundaries of the human α-tropomyosin gene (FIG. 1, middle panel). Nine primer pairs were constructed that corresponded to human intron sequences flanking relevant exons. Striated muscle exons 1a, 2b, 3, 4, 5, 6b, 7, 8, and 9a, b of the α-tropomyosin gene were PCR amplified from peripheral blood lymphocyte DNAs of two affected and two unaffected individuals from each family. Amplified products were then analyzed by cycle sequencing (Materials and Methods). No sequence abnormalities were detected in eight exons amplified from family members with FHC (data not shown). Unique sequence abnormalities were detected in exon 5 derived from affected individuals from each family.

Figure 2:
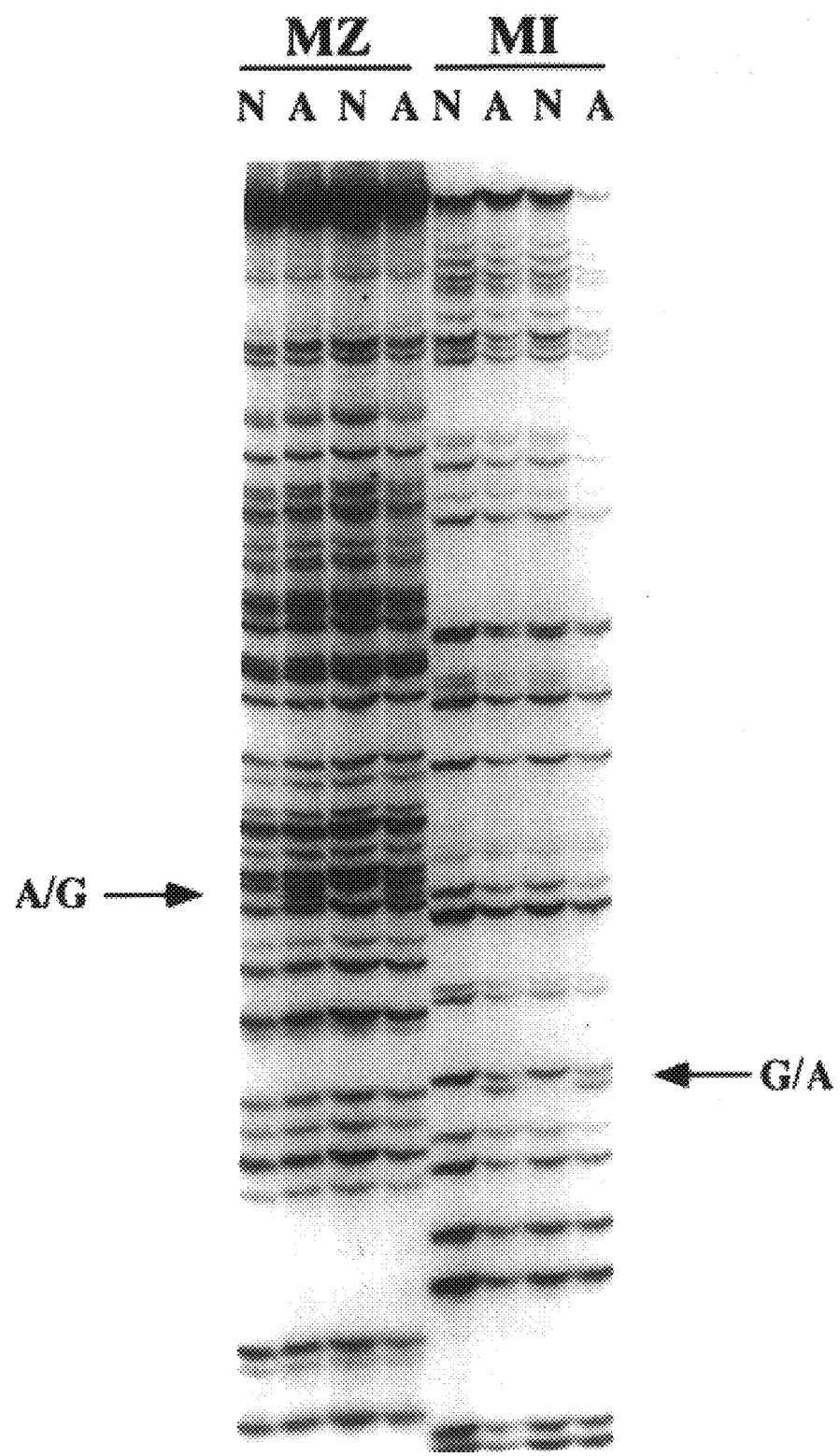
FIG. 2 depicts a mutation analysis of exon 5 of the α-tropomyosin gene. Exon 5 was amplified from genomic DNA and analyzed by cycle sequencing reactions from normal (N) and affected (A) individuals. The products of the dideoxy guanine reaction are shown for family MZ; affected individuals were heterozygous at nucleotide residue 595 (arrow). The products of the dideoxy adenine reaction are shown for family MI; affected individuals are heterozygous at nucleotide 579 (arrow).

Affected members of family MZ had a guanine residue at nucleotide position 595 in exon 5 of the α-tropomyosin gene (FIG. 2, left). The normal adenine residue was also present at position 595, demonstrating that all affected individuals in family MZ were heterozygous, while all unaffected family members were homozygous. This A→G transition changes codon180 from GAG to GGG and predicts that a negatively charged glutamic acid residue is replaced by a neutral glycine residue (Table 1).

A sequence abnormality was also identified in exon 5 amplified from DNA derived from affected individuals of family MI. In addition to the guanine residue at nucleotide position 579 seen in unaffected individuals, all affected members in this family also had an adenine residue (FIG. 2, right). This G→A transition alters codon 175 from GAC to AAC, thereby predicting that the mutated allele present in affected individuals will encode a neutral asparagine residue instead of the negatively charged aspartic acid residue found in unaffected individuals (Table 1).

Figure 3A:
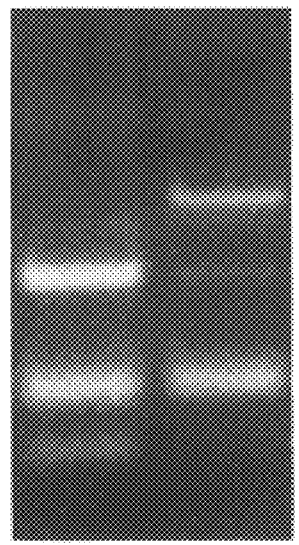
FIG. 3 depicts a confirmation analysis of mutations in the α-tropomyosin gene. Exon 5 was amplified from DNA derived from individuals in families MZ and MI. Samples were digested with Mn1I and size separated by gel electrophoresis (Panel A). The mutation at nucleotide residue 595 abolishes an Mn1I restriction enzyme site in an affected individual (A) and creates a 151 bp fragment in addition to fragments of 105, 58, and 46 bp found in a normal individual (N). Sequence analyses of 2 clones of exon 5, derived from one affected member of family MI are shown in the Panel B. Heterozygosity of the affected individual is demonstrated at residue 579 (arrow). The normal allele has a guanine residue; the affected allele has an adenine residue.
Figure 3B:
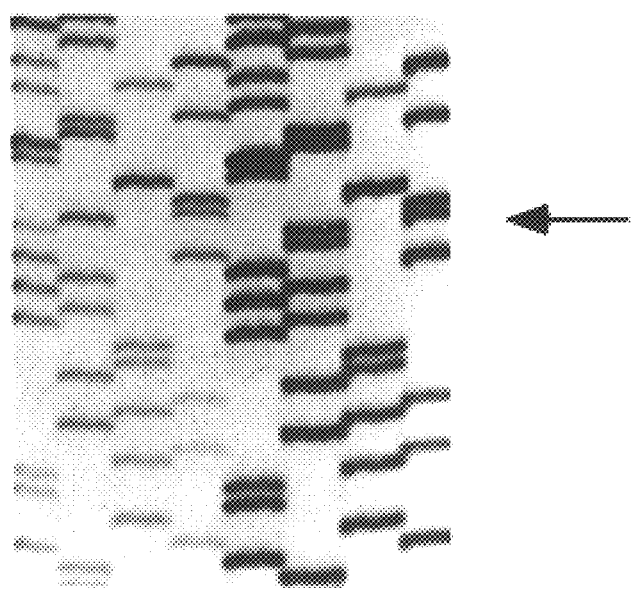

The nucleotide sequence abnormalities identified in affected members from families MZ and MI were confirmed by independent approaches. The A→G transition observed in affected members of family MZ predicts that an MnlI restriction enzyme site at nucleotide position 588 will be abolished. Exon 5 was amplified from DNA derived from an affected and an unaffected individual and digested with MnlI (FIG. 3, Panel A). Because the affected individual is heterozygous, both the normal digestion pattern (fragments sized 105, 58, and 46 bp) and an additional 151 bp fragment are present. The latter is not found in DNA derived from an unaffected individual. The sequence variant found in affected members of family MI did not alter a restriction enzyme site. To confirm this abnormality, exon 5 was amplified from DNA derived from an affected individual and subcloned. Ten independent plasmid clones were isolated and sequenced. Four clones contained the normal guanine residue at nucleotide 579, derived from the normal allele while six clones contained an adenine residue derived from the affected allele (FIG. 3, Panel B).

To determine whether the sequence variations found in exon 5 of the α-tropomyosin gene in individuals with FHC from families MZ and MI were common polymorphisms, this exon was amplified from more than 200 normal chromosomes and analyzed by cycle sequencing (data not shown). While a rare polymorphism (T→G transversion at nucleotide position 605, FIG. 1) that did not change the amino acid sequence was identified in one healthy individual, neither of the sequence variations found in affected individuals from families MZ and MI were present in normal chromosomes.

Sequence abnormalities identified in affected members of both families occur in exon 5. Nucleotide and amino acid sequences of exon 5 are available from the rat (Ruiz-Opazo, N. and Nadal-Ginard, B. (1987) *J. Biol. Chem.* 262:4755–4765), mouse (Takenaga, K. et al. (1988) *Mol. Cell. Biol.* 8:5561–5565), and frog (Hardy, S. et al. (1991) *Eur. J. Biochem.* 202:431–440). Comparison of these sequences demonstrates marked amino acid conservation among these species (Table 1). There is also sequence homology between the human α- and β-tropomyosin genes (Prasad, G. L. et al. (1991) *Biochem. Biophys. Res. Commun.* 177:1068–1075); the amino acid sequences of exon 5 differ only by conservative amino acid substitutions (Table

TABLE 1

Conservation of α-Tropomyosin Residues Affected by Missense Mutations

| | |
|---|---|
| 1) Human α-Tropomyosin (MacLeod, A.R. and Gooding, C. (1988) Mol. Cell. Biol. 8:433–440) | VARKLVIIESDLERAEERAELSEG (SEQ ID NO: 26) |
| 2) Family MZ | VARKLVIIESDLERA(G)ERAELSEG (SEQ ID NO: 27) |
| 3) Family MI | VARKLVIIES(N)LERAEERAELSEG (SEQ ID NO: 28) |
| 4) Mouse α-Tropomyosin (Takenaga, K. et al. (1989) Mol. Cell. Biol. 8:5561–5565) | VARKLVIIESDLERAEERAELSEG (SEQ ID NO: 26) |
| 5) Rat α-Tropomyosin (Ruiz-Opazo, N. and Nadal-Ginard, B. (1987) J. Biol. Chem. 262:4755–4765) | VARKLVIIESDLERAEERAELSEG (SEQ ID NO: 26) |
| 6) Xenopus α-Tropomyosin (Hardy, S. et al. (1991) Eur. J. Biochem. 202:431–440) | VARKLVIIE(G)DLERAEERAELSEG (SEQ ID NO: 29) |
| 7) Human β-Tropomyosin (Prasad, G.L. et al. (1991) Biochem. Biophys. Res. Commun. 177:1068–1075) | VARKLVI(L)E(GE)LER(S)EERAE(VA)E(S) (SEQ ID NO: 30) |

1). The demonstration of sequence abnormalities in a region of the α-tropomyosin gene that has been conserved during evolution suggests a functional consequence to the changes identified in individuals with FHC.

EXAMPLE 2
IDENTIFICATION OF MUTATIONS IN THE CARDIAC TROPONIN T GENE

Mapping the human cardiac troponin T gene to CMH2

The identification of FHC-causing mutations in the α-tropomyosin gene implicated other components of the thin filament as candidate genes at other FHC loci. To determine the genomic location of human cardiac troponin T, oligonucleotide primers flanking a 108 bp fragment of the 3' untranslated region of the cDNA (Mesnard, L. et al. (1993) *FEBS Lett.* 328:139–144) were synthesized. These primers were used to amplify DNA derived from somatic human×Chinese hamster cell hybrids using PCR. The 108 bp fragment was amplified only from 3 hybrids, each of which contained the long arm of human chromosome 1 (Materials and Methods; data not shown). The cardiac troponin T gene, like CMH2, therefore, is located on chromosome 1q.

Cardiac troponin T mRNAs derived from individuals in families with CMH2-linked FHC were screened by RNase A protection assays (Materials and Methods). Two overlapping fragments (nucleotide residues 1–570 and 523–915) of cardiac troponin T cDNA were amplified from lymphocyte cDNA by two nested rounds of PCR. RNase A protection assays of the 570 bp fragment of cardiac troponin T cDNA revealed a different pattern in some samples amplified from both affected and unaffected individuals (data not shown). To determine the nucleotide sequence difference that accounted for this pattern, the 570 bp fragment was analyzed by cycle sequencing. A T→C polymorphism at cDNA nucleotide residue 330 (FIG. 4) was identified. This polymorphism did not alter the encoded amino acid, but did abolish a TaqI restriction enzyme site. By comparison to the rat genomic structure (Jin, J. P. et al. (1992) *J. Mol. Biol.* 227:1269–1276), this sequence was predicted to be in exon 9. The TaqI restriction fragment length polymorphism (RFLP) was used to assess linkage between CMH2 and the cardiac troponin T gene in family AU (Watkins, H. et al. (1993) *Nature Genet.* 3:333–337), with FHC linked to CMH2. A maximum two point lod score of 6.3 ($\theta$=0) was achieved, indicating odds of 2,000,000:1 in favor of linkage between the cardiac troponin T gene and CMH2.

Identification of a cardiac troponin T splice donor sequence mutation

RNase A protection assays of the entire cardiac troponin T cDNA derived from individuals in family AU demonstrated abnormalities only in fragment 523-915. The normal (392 bp) and a smaller fragment (351 bp) were amplified from samples of affected individuals (data not shown). The smaller fragment was subcloned and nucleotide sequence analyses demonstrated that 41 consecutive nucleotides (residues 793–833, FIG. 5, Panel C) were absent. Comparison with the rat genomic sequence (Jin, J. P. et al. (1992) *J. Mol. Biol.* 227:1269–1276) indicated that these deleted sequences comprised exon 15.

Amplification of cDNAs derived from affected members of Family AU using oligonucleotide primers 769F and 880R (FIG. 4 and Materials and Methods) identified an additional aberrant cardiac troponin T transcript. The normal cDNA fragment (111 bp), a 70 bp fragment (corresponding to loss of exon 15) and a 124 bp fragment were detected (FIG. 5, Panel A). Nucleotide sequence analyses of the 124 bp cDNA product revealed thirteen novel nucleotide residues inserted between residues corresponding to the 3' end of exon 15 and the start of exon 16 (FIG. 5, Panel C). The quantity of the two aberrant transcripts appeared comparable (estimated by ethidium bromide staining), and combined were of similar quantity to the normal transcript amplified from affected individuals.

The translation of both these transcripts predicted abnormal cardiac troponin T molecules (FIG. 5, Panel C, mutant cDNAs). The shorter cDNA (FIG. 5, Panel A, 70 bp fragment) encodes a truncated polypeptide, due to a frameshift that results in premature termination. Twenty eight amino acids encoded by exons 15 and 16 would be replaced by seven novel residues prior to termination at a TAA codon. The longer cDNA (124 bp fragment, FIG. 5, Panel A) encodes a premature termination signal after the normal amino acid residues of exon 15, resulting in the loss of the 14 terminal amino acid residues.

Abnormal mRNAs detected in samples from affected members of family AU most likely resulted from abnormal splice donor or acceptor sequences in the cardiac troponin T gene. Because neither the structure nor sequence of the normal human cardiac troponin T gene was known, oligonucleotide primers were designed from cDNA sequences (796F, 823R; 793F, 880R; FIG. 4 and Materials and Methods) to amplify introns 14 and 15 from genomic DNA. A portion of these intron sequences was determined by cycle sequencing. Additional primers were then designed (I14R, I14F, I15R, FIG. 4 and Materials and Methods) to precisely define the sequences at intron/exon boundaries. The 5' and 3' sequences of intron 14 were identical in samples derived from an affected and unaffected individual from family AU. In contrast, both the normal intron 15 sequence and a G→A transition in the exon 15 splice donor site (FIG. 5, Panel B) was present in the affected individual. This change in the splice donor sequence (GTAAGT to ATAAGT) accounts for the two aberrant splice products found in affected individuals. Skipping of exon 15 results in the shorter cardiac troponin r cDNA. Activation of a cryptic splice site in intron 15 results in the insertion of the first 13 nucleotides from intron 15 into the cDNA sequence, resulting in the longer product (FIG. 5, Panel A and FIG. 5, Panel B).

The presence or absence of an adenine residue at position 1 of intron 15 was determined using DNA derived from all members of family AU and more than 100 unrelated individuals (Materials and Methods). The G→A transition in the splice donor sequence was found in every affected adult in family AU and in three clinically unaffected adults who are known to carry the disease haplotype at multiple polymorphic markers (Watkins, H. et al. (1993) *Nature Genet.* 3:333–337). The G→A transition was not present in other clinically unaffected adults in family AU nor in over 200 normal chromosomes derived from unrelated normal individuals. Linkage between the G→A transition and FHC in family AU was assessed by calculation of lod scores. Assuming an allele frequency of 0.01, and scoring the non-penetrant adults as unknown phenotype, a two point lod score of 11.8 at $\theta$=0 was calculated.

Identification of cardiac troponin T missense mutations

Cardiac troponin T transcripts were studied in two other families with FHC linked to CMH2 by RNase A protection assays (Materials and Methods). No sequence abnormalities were detected in fragment 523-915 by RNase protection assays. Novel ribonuclease protection products were identified in fragment 1-570 amplified from affected individuals in both families (data not shown). Because the fragment amplified from affected individuals was of normal size, single nucleotide differences most likely accounted for the abnormalities in RNase A protection assays.

Figure 6A:
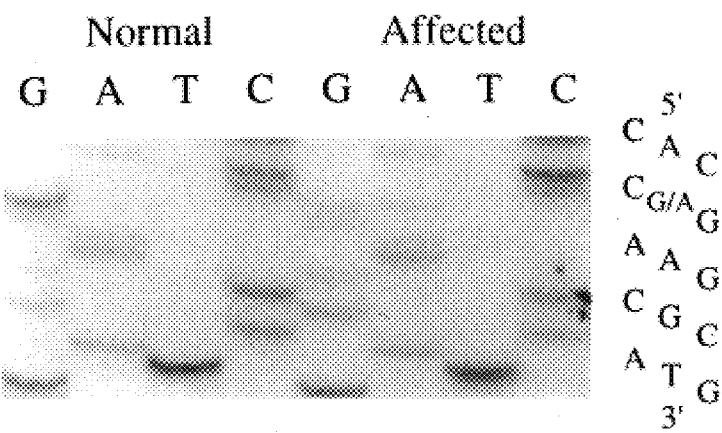
FIG. 6 Panels A–C, show cardiac troponin T missense mutations. Panel A depicts the genomic nucleotide sequence of exon 9 from a normal and an affected individual in family BA. The affected individual is heterozygous for a G→A transition at position 287, encoding an Arg92Gln substitution. Panel B shows an analysis confirming the G287A mutation by MspI digest in affected (A) and normal (N) members of family BA. Exons 8 and 9 were amplified with primers 214F and 393R. In the mutant allele, an MspI site 105 bp 5' from the end of exon 9 is abolished. U=uncut, M=size marker (#X174/HaeIII). Panel C shows an analysis confirming the T248A (Ile79Asn) mutation by Sau3A digest in affected (A) and normal (N) members of family AW. Exon 8 was amplified with primers 214F and 276R. The T248A transversion abolishes a Sau3A site resulting in an intact 62 bp fragment, rather than the 35 and 27 bp fragments (not resolved on this gel) of the normal allele.
Figure 6B:
Figure 6C:
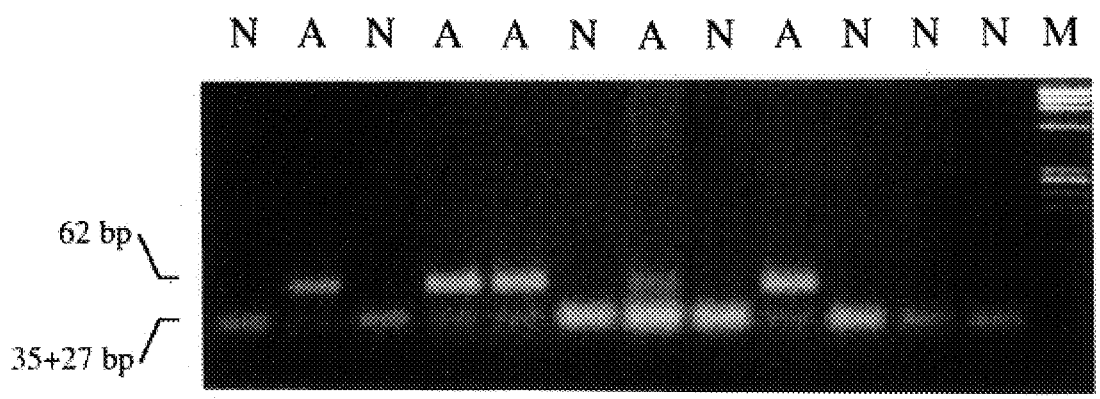

The cDNA fragment 1-570 was amplified from an affected member of family BA and analyzed by cycle sequencing. Both the normal guanine residue and an adenine residue were found at nucleotide residue 287 (FIG. 6, Panel A). This G287A transition changes codon 92 from CGG to CAG, predicting the replacement of a positively charged arginine with a neutral glutamine (designated Arg92Gln). The G287A transition abolishes an MspI site present in cDNA. By comparison to the rat genomic structure (Jin, J.

P. et al. (1992) *J. Mol. Biol.* 227:1269–1276), this sequence should be encoded in human exon 9. Primers were constructed (214F, 393R; FIG. 4, Panel A) to amplify a 500 bp fragment (containing exons 8 and 9) of genomic DNA derived from all members of family BA. Samples were digested with MspI to test for the presence or absence of the Arg92Gln allele. All affected individuals had the G287A allele in family BA (FIG. 6, Panel B).

Sequence analysis of the cDNA fragment 1-570 amplified from affected members in family AW demonstrated both a normal allele and an allele with a T→A transversion at residue 248. The T248A transversion would be expected to change codon 79 from ATC to AAC thereby replacing the normal non-polar isoleucine with a polar asparagine residue (designated Ile79Asn). T248A abolishes a Sau3A restriction enzyme site. Codon 79 is in exon 8 of the rat gene (Jin, J. P. et al. (1992) *J. Mol. Biol.* 227:1269–1276), suggesting that this sequence should be encoded in human exon 8. A 62 bp fragment containing exon 8 was amplified (FIG. 4, Panel A) from genomic DNA derived from all members of family AW and digested with Sau3A to test for the T248A transversion. All affected members of family AW had the T248A allele (FIG. 6, Panel C).

Neither the Arg92Gln or Ile79Asn allele was found in unaffected family members or in DNAs derived from 200 normal chromosomes. Linkage between FHC and these sequence variants was assessed by calculating lod scores, assuming that the frequency of the disease-associated allele was 0.01. The maximum two point lod score in family BA=4.1 (θ=0); in family AW=2.0 (θ=0).

These results demonstrate that mutations in the α-tropomyosin or cardiac troponin T genes cause FHC in 5 families. This conclusion is supported by four lines of evidence. First, the α-tropomyosin gene is closely liked to the CMG3 locus (maximum combined lod score=6.9, θ=0) and cardiac troponin T is closely linked to CMH2 (maximum combined lod score=17.9, θ=0). Second, the nucleotide changes identified were present in all clinically affected individuals from 5 families. Third, none of these abnormalities were present in over 200 chromosomes from unrelated normal individuals. Fourth, the encoded amino acid substitutions in each gene are predicted to cause a significant change in the structure and/or function of the encoded polypeptide. The α-tropomyosin mutations Glu180Gly and Asp175Arg occur at residues that have been highly conserved throughout evolution (Table 1) and alter the charge of the encoded amino acid. The Ile79Asn missense in cardiac troponin T affects a residue that is conserved in all known vertebrate troponin T sequences; the Arg92Gln mutation substitutes an uncharged residue at a position invariably occupied by a basic residue in vertebrate troponin T sequences (Table 2). The 5' splice donor site mutation of intron 15 produces markedly aberrant cardiac troponin T mRNA transcripts. Collectively these findings define the molecular etiology of FHC and can provide insights into the pathophysiology of non-heritable forms of cardiac hypertrophy.

TABLE 2

Conservation of Troponin T (TnT) Residues Affected by Missense Mutations

| | |
|---|---|
| 1) Human cardiac TnT (Mesnard, L. et al. (1993) FEBS Lett. 328:139–144) | MPNLVPPKIPDGERVDFDDIHRKRM (SEQ ID NO: 31) |
| 2) Family AW | MPNLVPPK(N)PDGERVDFDDIHRKRM (SEQ ID NO: 32) |
| 3) Family RA | MPNLVPPKIPDGERVDFDDIH(Q)KRM (SEQ ID NO: 33) |
| 4) Sheep cardiac TnT (McAuliffe, J.J. and Robbins, J. (1991) Pediatr. Res. 29:580–585) | MPNLVPPKIPDGERVDFDDIHRKRM (SEQ ID NO: 31) |
| 5) Bovine cardiac TnT (Lesyk, J. et al. (1987) Biochemistry 26:7035–7042) | MPNLVPPKIPDGERVDFDDIHRKRM (SEQ ID NO: 31) |
| 6) Rat cardiac TnT (Jin, J.P. and Lin, J.J. (1989) J. Biol. Chem. 264:14471–14477) | MPNLVPPKIPDGERVDFDDIHRKRM (SEQ ID NO: 31) |
| 7) Rabbit cardiac TnT (Pearlstone, J.R. et al. (1986) J. Biol. Chem. 2267:16796–16810) | MPNLVPPKIPDGERVDFDDIHRKRM (SEQ ID NO: 31) |
| 8) Chicken cardiac TnT (Cooper, T.A. and Ordahl, C.P. (1985) J. Biol. Chem. 26:11140–11148) | MPNLVPPKIPDGER(L)DFDDIHRKRM (SEQ ID NO: 34) |
| 9) Human slow cardiac TnT (Gahlmann, R. et al. (1987) J. Biol. Chem. 262:16122–16126) | (V)P(P)L(I)PPKIP(E)GERVDFDDIHRKRM (SEQ ID NO: 35) |
| 10) Rat fast skeletal cardiac TnT (Breitbart, R.E. and Nadal-Ginard, B. (1986) J. Mol. Biol. 188:313–324) | - - - L(TA)PKIP(E)GE(K)VDFDDI(QK)KR(Q) (SEQ ID NO: 36) |
| 11) Rabbit fast skeletal cardiac TnT (Pearlstone, J.R. et al. (1977) J. Biol. Chem. 252:983–989) | - - - L(TA)PKIP(E)GE(K)VDFDDI(QK)KR(Q) (SEQ ID NO: 36) |
| 12) Chicken fast skeletal cardiac TnT (Smillie, L.B. et al. (1988) J. Biol. Chem. 263:18816–18820) | - - - L(TA)PKIP(E)GE(K)VDFDDI(QK)KR(Q) (SEQ ID NO: 36) |
| 13) Quail fast skeletal cardiac TnT (Bucher, E.A. et al. (1989) J. Biol. Chem. 264:12482–12491) | - - - L(TA)PKIP(E)GE(K)VDFDDI(QK)KR(Q) (SEQ ID NO: 36) |

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A method for detecting the presence or absence of a mutation in a subject in need of diagnosis for hypertrophic cardiomyopathy, comprising:
   providing DNA from the subject which encodes α-tropomyosin or cardiac troponin T protein; and
   detecting the presence or absence of a mutation in the DNA which is associated with hypertrophic cardiomyopathy.

2. The method of claim 1 further comprising amplifying the DNA to form an amplified product and detecting the presence or absence of a mutation in the amplified product which is associated with hypertrophic cardiomyopathy.

3. The method of claim 2 further comprising providing DNA encoding β cardiac myosin heavy chain and detecting the presence or absence of a mutation in the DNA which is associated with hypertrophic cardiomyopathy.

4. The method of claim 1 wherein the hypertrophic cardiomyopathy is familial hypertrophic cardiomyopathy.

5. The method of claim 1 wherein the hypertrophic cardiomyopathy is sporadic hypertrophic cardiomyopathy.

6. The method of claim 1 wherein the mutation is a point mutation.

7. The method of claim 6 wherein the point mutation is a missense mutation.

8. The method of claim 1 wherein the mutation in cardiac troponin T is a 5' splice site donor mutation.

9. The method of claim 1 wherein the DNA which encodes an α-tropomyosin or cardiac troponin T protein is cDNA reversed transcribed from RNA.

10. The method of claim 9 wherein the RNA is obtained from nucleated blood cells.

11. The method of claim 1 wherein the presence or absence of the mutation in a subject in need of diagnosis for hypertrophic cardiomyopathy is detected by contacting the DNA with an RNA probe completely hybridizable to DNA which encodes a normal α-tropomyosin or cardiac troponin T protein to form a hybrid double strand having an RNA and DNA strand, the hybrid double strand having an unhybridized portion of the RNA strand at any portion corresponding to a hypertrophic cardiomyopathy-associated mutation in the DNA strand; and
   detecting the presence or absence of an unhybridized portion of the RNA strand as an indication of the presence or absence of a hypertrophic cardiomyopathy-associated mutation in the corresponding portion of the DNA strand.

12. The method of claim 4 wherein the presence or absence of the mutation in a subject in need of diagnosis for familial hypertrophic cardiomyopathy is detected by contacting the DNA with an RNA probe completely hybridizable to DNA which encodes a normal α-tropomyosin or cardiac troponin T protein to form a hybrid double strand having an RNA and DNA strand, the hybrid double strand having an unhybridized ribonucleotide of the RNA strand at any portion corresponding to a familial hypertrophic cardiomyopathy associated point mutation in the DNA strand;
   contacting the hybrid double strand with an agent capable of digesting an unhybridized portion of the RNA strand; and
   detecting the presence or absence of an unhybridized ribonucleotide of the RNA strand as an indication of the presence or absence of a familial hypertrophic cardiomyopathy associated point mutation in the corresponding deoxyribonucleotide of the DNA strand.

13. The method of claim 2 wherein the DNA which encodes an (α-tropomyosin or cardiac troponin T protein is amplified.

14. The method of claim 13 wherein the DNA is amplified using a polymerase chain reaction.

15. A method for diagnosing familial hypertrophic cardiomyopathy in a subject, comprising:
   obtaining a sample of DNA which encodes an α-tropomyosin or cardiac troponin T protein from a subject being tested for familial hypertrophic cardiomyopathy;
   diagnosing the subject for familial hypertrophic cardiomyopathy by detecting the presence or absence of a mutation in the α-tropomyosin or cardiac troponin T protein which causes familial hypertrophic cardiomyopathy as an indication of the disease.

16. A non-invasive method for diagnosing hypertrophic cardiomyopathy, comprising:

obtaining a blood sample from a subject being tested for hypertrophic cardiomyopathy;

isolating RNA encoding α-tropomyosin or cardiac troponin T protein from the blood sample; and diagnosing the subject for hypertrophic cardiomyopathy by detecting the presence or absence of a mutation in the RNA which is associated with hypertrophic cardiomyopathy as an indication of the disease.

17. The method of claim 16 wherein the presence or absence of a mutation associated with hypertrophic cardiomyopathy in the RNA is detected by preparing α-tropomyosin or cardiac troponin T protein cDNA from the RNA to form α-tropomyosin or cardiac troponin T DNA and detecting mutations in the DNA as being indicative of mutations in the RNA.

18. The method of claim 16 further comprising amplifying the α-tropomyosin or cardiac troponin T DNA prior to detecting a mutation in the DNA which is associated with hypertrophic cardiomyopathy.

19. The method of claim 16 wherein the hypertrophic cardiomyopathy is familial hypertrophic cardiomyopathy.

20. The method of claim 16 wherein the hypertrophic cardiomyopathy is sporadic hypertrophic cardiomyopathy.

21. The method of claim 16 futher comprising evaluation te subject for clinical symptoms associated with hypertrophic cardiomyopathy.

22. A kit useful for diagnosing hypertrophic cardiomyopathy, comprising:

a first container holding an RNA probe completely hybridizable to DNA which encodes an α-tropomyosin or cardiac troponin T protein;

a second container holding primers useful for amplifying the DNA which encodes an α-tropomyosin or cardiac troponin T protein; and instructions for using the probe and primers for facilitating the diagnosis of hypertrophic cardiomyopathy.

23. A kit of claim 22 further comprising a third container holding an agent for digesting unhybridized RNA.

24. The kit of claim 22 further comprising instructions for using the components of the kit to detect the presence or absence of mutations in amplified DNA which encodes α-tropomyosin or cardiac troponin T protein.

\* \* \* \* \*

UNITED STATES PATENT AND TRADEMARK OFFICE
CERTIFICATE OF CORRECTION

PATENT NO. : 5,912,121
DATED : June 15, 1999
INVENTOR(S) : Christine Seidman et al.

It is certified that error appears in the above-identified patent and that said Letters Patent is hereby corrected as shown below:

Title page, item [73] should read --
--[73] Assignees: Brigham and Women's Hospital, Brookline; President and Fellows of Harvard College, Cambridge, both of Mass.

Signed and Sealed this

Seventh Day of December, 1999

Attest:

Q. TODD DICKINSON

*Attesting Officer*     *Acting Commissioner of Patents and Trademarks*

```
                           SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

AGCTGGATGT CCCACCTCT                                                      19

(2) INFORMATION FOR SEQ ID NO:2:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

ACGAAGAGCT TCTGTACAAT AG                                                  22

(2) INFORMATION FOR SEQ ID NO:3:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

GAGTCAGATG TTCCAATAAG GTAGG                                               25

(2) INFORMATION FOR SEQ ID NO:4:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

TGTCTTGCTC CCTACCCTCT GTGA                                                24

(2) INFORMATION FOR SEQ ID NO:5:

(i) SEQUENCE CHARACTERISTICS:
         (A) LENGTH: 29 base pairs
         (B) TYPE: nucleic acid
         (C) STRANDEDNESS: single
         (D) TOPOLOGY: linear
```

-continued (ii) MOLECULE TYPE: cDNA (xi) SEQUENCE DESCRIPTION: SEQ ID NO:5:

CCGGAATTCT GCTGCAGCCC CAGGCCCCT                                   29

(2) INFORMATION FOR SEQ ID NO:6:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:6:

GGTGCCAGGC TCGAGTCCCG                                             20

(2) INFORMATION FOR SEQ ID NO:7:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:7:

TCCCTGTACC CCCTGGCCAA                                             20

(2) INFORMATION FOR SEQ ID NO:8:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:8:

CGCGGATCCG GGAAGCAGTG TGAGCGTGC                                   29

(2) INFORMATION FOR SEQ ID NO:9:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:9:

CCCAGCCATT TCCTGAAGCT ACCA                                        24

(2) INFORMATION FOR SEQ ID NO:10:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:10:

```
CCACCAGGAA AGGCAGCTGC AAAAG                                              25
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
GGCCACAGCA GTGCAGTGTG CATTT                                              25
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GGCTGTCCTG AAGGCCACTG CT                                                 22
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
CCATGCCCTT CTGTTACACA AAGC                                               24
```

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
TGCCAGAAGG TCATGCTGTT TAGTC                                              25
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
TTGGCTTGTC TCCCACCCTT                                                    20
```

(2) INFORMATION FOR SEQ ID NO:16:

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGCCTCTTTT GAGCAGCTCT TAAAAG                                       26

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GAGTAGATTG AGCAGCAGCT TGACA                                        25

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

ATGAAAAGGC CTGACCGGTT CCATG                                        25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CCCTATGTTT GTAGCTACAG GAAAC                                        25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AGTGCAAAGG AGCGTATCAA TGTGG                                        25

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:21:

TCTGCCTTCC ACTTCCTGGT                                                          20

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CAAGGAGGCA TGGTGGTGAG TTTA                                                     24

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CCCAGGGACC TGCAGCAGTA TTACC                                                    25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TCAGCTCCAC GTTGCTCTTT GTCCT                                                    25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

AAGGAGGAAT GGGATAGCTG GAAGG                                                    25

(2) INFORMATION FOR SEQ ID NO:26:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

```
    Val Ala Arg Lys Leu Val Ile Ile Glu Ser Asp Leu Glu Arg Ala Glu
    1               5                   10                  15

Glu Arg Ala Glu Leu Ser Glu Gly
                20
```

(2) INFORMATION FOR SEQ ID NO:27:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

```
    Val Ala Arg Lys Leu Val Ile Ile Glu Ser Asp Leu Glu Arg Ala Gly
    1               5                   10                  15

Glu Arg Ala Glu Leu Ser Glu Gly
                20
```

(2) INFORMATION FOR SEQ ID NO:28:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:28:

```
    Val Ala Arg Lys Leu Val Ile Ile Glu Ser Asn Leu Glu Arg Ala Glu
    1               5                   10                  15

Glu Arg Ala Glu Leu Ser Glu Gly
                20
```

(2) INFORMATION FOR SEQ ID NO:29:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

```
    Val Ala Arg Lys Leu Val Ile Ile Glu Gly Asp Leu Glu Arg Ala Glu
    1               5                   10                  15

Glu Arg Ala Glu Leu Ser Glu Gly
                20
```

(2) INFORMATION FOR SEQ ID NO:30:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

```
        Val Ala Arg Lys Leu Val Ile Leu Glu Gly Glu Leu Glu Arg Ser Glu
        1               5                  10                  15

Glu Arg Ala Glu Val Ala Glu Ser
                    20
```

(2) INFORMATION FOR SEQ ID NO:31:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

```
        Met Pro Asn Leu Val Pro Pro Lys Ile Pro Asp Gly Glu Arg Val Asp
        1               5                  10                  15

Phe Asp Asp Ile His Arg Lys Arg Met
                    20                  25
```

(2) INFORMATION FOR SEQ ID NO:32:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

```
        Met Pro Asn Leu Val Pro Pro Lys Asn Pro Asp Gly Glu Arg Val Asp
        1               5                  10                  15

Phe Asp Asp Ile His Arg Lys Arg Met
                    20                  25
```

(2) INFORMATION FOR SEQ ID NO:33:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

```
        Met Pro Asn Leu Val Pro Pro Lys Ile Pro Asp Gly Glu Arg Val Asp
        1               5                  10                  15

Phe Asp Asp Ile His Gln Lys Arg Met
                    20                  25
```

(2) INFORMATION FOR SEQ ID NO:34:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

```
   Met Pro Asn Leu Val Pro Pro Lys Ile Pro Asp Gly Glu Arg Leu Asp
   1               5                   10                  15

Phe Asp Asp Ile His Arg Lys Arg Met
                   20                  25
```

(2) INFORMATION FOR SEQ ID NO:35:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

```
   Val Pro Pro Leu Ile Pro Pro Lys Ile Pro Glu Gly Glu Arg Val Asp
   1               5                   10                  15

Phe Asp Asp Ile His Arg Lys Arg Met
                   20                  25
```

(2) INFORMATION FOR SEQ ID NO:36:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

```
   Leu Thr Ala Pro Lys Ile Pro Glu Gly Glu Lys Val Asp Phe Asp Asp
   1               5                   10                  15

Ile Gln Lys Lys Arg Gln
                   20
```

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..12

(xi) SEQUENCE DESCRIPTION: SEQ ID NO:37:

```
CAG AAA TAT GAG GTGGCCGCCA TGCTGTCCCC                            32
Gln Lys Tyr Glu
  1
```

(2) INFORMATION FOR SEQ ID NO:38:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:38:

Gln Lys Tyr Glu
1

(2) INFORMATION FOR SEQ ID NO:39:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 21..62

(xi) SEQUENCE DESCRIPTION: SEQ ID NO:39:

```
CCTTCCCACT TTTCTTGCAG ATC AAT GTT CTC CGA AAC AGG ATC AAC GAT        50
                     Ile Asn Val Leu Arg Asn Arg Ile Asn Asp
                      1               5                  10

AAC CAG AAA GT GTAAGTGTCT GAGGTCATTC                                 81
Asn Gln Lys Val
```

(2) INFORMATION FOR SEQ ID NO:40:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:40:

```
Ile Asn Val Leu Arg Asn Arg Ile Asn Asp Asn Gln Lys Val
 1               5                  10
```

(2) INFORMATION FOR SEQ ID NO:41:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 21..63

(xi) SEQUENCE DESCRIPTION: SEQ ID NO:41:

```
GCGTCCTGCT TCCCCTGCAG C TCC AAG ACC CGC GGG AAG GCT AAA GTC ACC      51
                       Ser Lys Thr Arg Gly Lys Ala Lys Val Thr
                        1               5                  10

GGG CGC TGG AAA TAGAGCCTGG CCTCCTTCAC CAA                            86
Gly Arg Trp Lys
```

(2) INFORMATION FOR SEQ ID NO:42:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:42:

```
Ser Lys Thr Arg Gly Lys Ala Lys Val Thr Gly Arg Trp Lys
 1               5                  10
```

(2) INFORMATION FOR SEQ ID NO:43:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..12

(xi) SEQUENCE DESCRIPTION: SEQ ID NO:43:

```
CAG AAA TAT GAG                                                        12
Gln Lys Tyr Glu
  1
```

(2) INFORMATION FOR SEQ ID NO:44:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:44:

```
Gln Lys Tyr Glu
  1
```

(2) INFORMATION FOR SEQ ID NO:45:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..21

(xi) SEQUENCE DESCRIPTION: SEQ ID NO:45:

```
CTC CAA GAC CCG CGG GAA GGC TAAAGTCACC GGGCGCTGGA AATAGAGCCT           51
Leu Gln Asp Pro Arg Glu Gly
  1               5
```

(2) INFORMATION FOR SEQ ID NO:46:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:46:

```
Leu Gln Asp Pro Arg Glu Gly
  1               5
```

(2) INFORMATION FOR SEQ ID NO:47:

(i) SEQUENCE CHARACTERISTICS:
        (A) LENGTH: 72 base pairs
        (B) TYPE: nucleic acid
        (C) STRANDEDNESS: single

```
            (D) TOPOLOGY: linear (ii) MOLECULE TYPE: cDNA (ix) FEATURE:
            (A) NAME/KEY: CDS
            (B) LOCATION: 1..42

(xi) SEQUENCE DESCRIPTION: SEQ ID NO:47:

ATC AAT GTT CTC CGA AAC AGG ATC AAC GAT AAC CAG AAA GTA              42
Ile Asn Val Leu Arg Asn Arg Ile Asn Asp Asn Gln Lys Val
 1               5                  10

TAAGTGTCTG AGCTCCAAGA CCCGCGGGAA                                     72

(2) INFORMATION FOR SEQ ID NO:48:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO:48:

Ile Asn Val Leu Arg Asn Arg Ile Asn Asp Asn Gln Lys Val
 1               5                  10
```